United States Patent
Soya et al.

(10) Patent No.: US 9,090,931 B2
(45) Date of Patent: Jul. 28, 2015

(54) METHOD FOR MEASURING GLYCATED HEMOGLOBIN

(75) Inventors: Haruyo Soya, Sunto-gun (JP); Tomomi Murakami, Sunto-gun (JP); Haruki Tsunoda, Sunto-gun (JP); Yu Ohsugi, Sunto-gun (JP); Ayako Yoda, Sunto-gun (JP); Masashi Matsushita, Sunto-gun (JP)

(73) Assignee: KYOWA MEDEX CO., LTD, Tokyo (JP)

( * ) Notice: Subject to any disclaimer, the term of this patent is extended or adjusted under 35 U.S.C. 154(b) by 100 days.

(21) Appl. No.: 13/811,914

(22) PCT Filed: Aug. 9, 2011

(86) PCT No.: PCT/JP2011/068104
§ 371 (c)(1),
(2), (4) Date: Jan. 24, 2013

(87) PCT Pub. No.: WO2012/020745
PCT Pub. Date: Feb. 16, 2012

(65) Prior Publication Data
US 2013/0115646 A1 May 9, 2013

(30) Foreign Application Priority Data
Aug. 11, 2010 (JP) ................. 2010-180563

(51) Int. Cl.
*C12Q 1/37* (2006.01)
*C12Q 1/26* (2006.01)
*C12Q 1/54* (2006.01)
*C12Q 1/28* (2006.01)
*G01N 33/72* (2006.01)
*G01N 21/78* (2006.01)

(52) U.S. Cl.
CPC .. *C12Q 1/37* (2013.01); *C12Q 1/26* (2013.01); *C12Q 1/28* (2013.01); *C12Q 1/54* (2013.01); *G01N 21/78* (2013.01); *G01N 33/723* (2013.01)

(58) Field of Classification Search
CPC .............. C12Q 1/37; C12Q 1/28; C12Q 1/26; C12Q 1/00; C12Q 1/46; C12Q 1/36; G01N 21/00; G01N 21/78; G01N 33/68; C07D 225/00; C07D 225/02
See application file for complete search history.

(56) References Cited

U.S. PATENT DOCUMENTS

| 5,384,248 | A | 1/1995 | Sakata et al. |
|---|---|---|---|
| 7,235,378 | B2 * | 6/2007 | Yonehara ..................... 435/14 |
| 2007/0154976 | A1 * | 7/2007 | Taniguchi et al. .............. 435/25 |
| 2008/0295259 | A1 | 12/2008 | Ueda et al. |

FOREIGN PATENT DOCUMENTS

| EP | 1 312 918 | 5/2003 |
|---|---|---|
| EP | 1 693 462 | 8/2006 |
| EP | 1 788 081 | 5/2007 |
| JP | 57-029297 | 2/1982 |
| JP | 62-093261 | 4/1987 |
| JP | 03-206896 | 9/1991 |
| JP | 2000-241405 | 9/2000 |
| JP | 2009-159989 | 7/2009 |
| WO | 03/107011 | 12/2003 |
| WO | 2004/007760 | 1/2004 |
| WO | 2005/049858 | 6/2005 |
| WO | 2005/088305 | 9/2005 |
| WO | 2006/013921 | 2/2006 |
| WO | WO 2007072941 A * | 6/2007 |
| WO | 2007/083703 | 7/2007 |

OTHER PUBLICATIONS

Hirokawa et al., BBRC, 311:104-111, 2003.*
AOYAMA, "H2O2-POD System", Journal of Medical Technology, vol. 41, No. 9 (1997) 1014-19.
"Standards of Medical Care in Diabetes", Diabetes Care, vol. 33, Suppl. 1 (2010) S11-17.
Diabetes World, vol. 4, No. 2 (2010) 56-65.

* cited by examiner

*Primary Examiner* — Jennifer McDonald
*Assistant Examiner* — Qing Xu
(74) *Attorney, Agent, or Firm* — Fitzpatrick, Cella, Harper & Scinto

(57) ABSTRACT

It is to provide a method for measuring glycated hemoglobin in a hemoglobin-containing sample, comprising: reacting glycated hemoglobin in the hemoglobin-containing sample with a proteolytic enzyme in the presence of at least one salt selected from the group consisting of a pyridinium salt, a phosphonium salt, an imidazolium salt, and an isoquinolinium salt; reacting the obtained reaction product with fructosyl peptide oxidase; and measuring the generated hydrogen peroxide. The present invention provides a method for accurately measuring glycated hemoglobin in a hemoglobin-containing sample.

5 Claims, 7 Drawing Sheets

METHOD FOR MEASURING GLYCATED HEMOGLOBIN

This application is a National Phase of PCT Application No. PCT/JP2011/068104 filed Aug. 9, 2011, which in turn claims benefit of Japanese Patent Application No. 2010-180563 filed Aug. 11, 2010.

TECHNICAL FIELD

The present invention relates to a method, a reagent, and a kit for measuring glycated hemoglobin in a hemoglobin-containing sample. The present invention further relates to a method for preserving an aqueous solution comprising a leuco chromogen and a method for stabilizing a leuco chromogen.

BACKGROUND ART

Glycated hemoglobin is a glycation product of hemoglobin in which glucose is bound thereto. Hemoglobin takes a tetrameric structure consisting of α and β chains. The glycated product of the N terminus of β chain of hemoglobon is called hemoglobin A1c, which increases with increase in blood glucose level and as such, is routinely measured as a diabetes mellitus marker for monitoring glycemic control in clinical laboratory examinations.

Known methods for measuring glycated hemoglobin include, for example, chromatography such as HPLC, electrophoresis, antibody-based immunoassay such as latex immunoagglutination assay, and enzymatic assay using an enzyme reactive to a glycated protein and an enzyme reactive to a glycated peptide and/or a glycated amino acid.

A known method for enzymatically measuring glycated hemoglobin comprises: first denaturing glycated hemoglobin in a hemoglobin-containing sample using a denaturant; reacting the denatured glycated hemoglobin with a proteolytic enzyme; subsequently reacting the generated glycated peptide with glycated peptide oxidase; reacting the generated hydrogen peroxide with a chromogen capable of developing color by oxidation in the presence of a peroxidatively active substance such as peroxidase to convert the chromogen to a dye; and measuring the glycated hemoglobin on the basis of the absorbance of the generated dye. In this context, the denaturant is used for reacting glycated hemoglobin with the proteolytic enzyme. Previously known denaturants are: a compound having an acetic acid group or a salt thereof, N-acyl taurine or a salt thereof, and polyoxyethylene alkyl ether sulfuric acid or a salt thereof (Patent Document 1); anionic surfactants such as polyoxyethylene alkyl ether sulfates and polyoxyethylene alkylphenyl ether sulfates (Patent Document 2); sodium lauryl sulfate and sulfonic acid compounds such as sodium dodecyl benzene sulfonate (Patent Document 3); sulfonic acid compounds and nitro compounds (Patent Document 4); quaternary ammonium salts, alkyl benzyl dimethyl ammonium chloride, lauryl dimethylamine oxide, and the like (Patent Document 5).

In a method for enzymatically measuring glycated hemoglobin, a method is often used which involves: converting glycated hemoglobin to hydrogen peroxide; reacting the generated hydrogen peroxide with a chromogen capable of developing color by oxidation in the presence of a peroxidatively active substance such as peroxidase to convert the chromogen to a dye; and measuring the glycated hemoglobin on the basis of the absorbance of the generated dye. In this context, a leuco chromogen is often used as the chromogen capable of developing color by oxidation. The leuco chromogen is a chromogen that generates a dye through reaction with hydrogen peroxide in the presence of a peroxidatively active substance such as peroxidase. This type of chromogen, unlike coupling-type chromogens, generates a dye in itself and known leuco chromogens include, for example, phenothiazine leuco chromogens, triphenylmethane leuco chromogens, and diphenylamine leuco chromogens (see e.g., Patent Documents 6 to 8).

The leuco chromogen is preferably used as a highly sensitive chromogen in the quantification of an analyte component, such as glycated hemoglobin, which is contained only in a trace amount in a sample (see e.g., Non-patent Document 1). The leuco chromogen, however, has poor preservation stability and undesirably develops color spontaneously with time, particularly, in a solution. The poor stability of this leuco chromogen disadvantageously causes the inaccurate measurement of an analyte component in a sample.

To cope with this undesirable poor stability of the leuco chromogen, methods for stabilizing the leuco chromogen in a solution have been studied and reported so far (see e.g., Patent Documents 9 and 10).

PRIOR ART DOCUMENTS

Patent Documents

Patent Document 1: WO2006/013921
Patent Document 2: WO2005/049858
Patent Document 3: WO2004/007760
Patent Document 4: WO2003/107011
Patent Document 5: Japanese unexamined Patent Application Publication No. 2009-159989
Patent Document 6: Japanese unexamined Patent Application Publication No. 57-029297
Patent Document 7: Japanese unexamined Patent Application Publication No. 3-206896
Patent Document 8: Japanese unexamined Patent Application Publication No. 62-093261
Patent Document 9: WO2005/088305
Patent Document 10: WO2007/083703

Non-Patent Documents

Non-patent Document 1: Journal of Medical Technology, 1997, Vol. 41, No. 9, p. 1014-1019

SUMMARY OF THE INVENTION

Problems to be Solved by the Invention

The previously known glycated hemoglobin denaturants used in the method for enzymatically measuring glycated hemoglobin do not sufficiently denature glycated hemoglobin. Use of such denaturants disadvantageously achieves neither satisfactory progression of proteolytic enzyme reaction nor accurate measurement of glycated hemoglobin. In addition, the previously known methods for preserving a leuco chromogen used in the method for measuring glycated hemoglobin are not always satisfactory, for example, because of requiring preservation under strict conditions.

An object of the present invention is to provide a method, a reagent, and a kit for accurately measuring glycated hemoglobin in a hemoglobin-containing sample, a method for preserving an aqueous solution containing a leuco chromogen, and a method for stabilizing such a leuco chromogen that enable accurate measurement of glycated hemoglobin in a hemoglobin-containing sample.

Means to Solve the Problems

The present inventors have conducted diligent studies on the problems and consequently found that glycated hemoglobin in a hemoglobin-containing sample is reacted with a proteolytic enzyme in the presence of a pyridinium salt, a phosphonium salt, an imidazolium salt, or an isoquinolinium salt, whereby hemoglobin and glycated hemoglobin can be denatured sufficiently while glycated hemoglobin in the hemoglobin-containing sample can be measured accurately. The present inventors have further found that the pyridinium salt, the phosphonium salt, the imidazolium salt, or the isoquinolinium salt stabilizes a leuco chromogen. On the basis of these findings, the present invention has been completed. Specifically, the present invention relates to the following [1] to [18]:

[1] A method for measuring glycated hemoglobin in a hemoglobin-containing sample, comprising: reacting glycated hemoglobin in the hemoglobin-containing sample with a proteolytic enzyme in the presence of at least one salt selected from the group consisting of a pyridinium salt represented by the following formula (I), a phosphonium salt represented by the following formula (II), an imidazolium salt represented by the following formula (III), and an isoquinolinium salt represented by the following formula (IV); reacting the obtained reaction product with fructosyl peptide oxidase; and measuring the generated hydrogen peroxide:

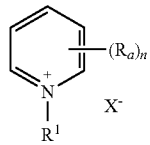
(I)

wherein $R^1$ represents a substituted or unsubstituted alkyl or a substituted or unsubstituted alkenyl; $R_a$ represents a hydrogen atom, a substituted or unsubstituted alkyl, or a substituted or unsubstituted alkenyl; n represents an integer of 1 to 5; and $X^-$ represents a monovalent anion;

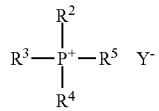
(II)

wherein $R^2$ to $R^5$ are the same or different, and each represents a substituted or unsubstituted alkyl; and $Y^-$ represents a monovalent anion;

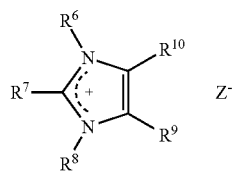
(III)

wherein $R^6$ and $R^8$ are the same or different, and each represents a substituted or unsubstituted alkyl or substituted or unsubstituted alkenyl; $R^7$, $R^9$, and $R^{10}$ each represents a hydrogen atom, a substituted or unsubstituted alkyl, or a substituted or unsubstituted alkenyl; and $Z^-$ represents a monovalent anion;

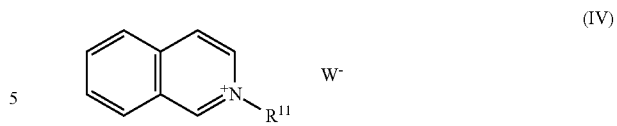
(IV)

wherein $R^{11}$ represents a substituted or unsubstituted alkyl or a substituted or unsubstituted alkenyl; and $W^-$ represents a monovalent anion.

[2] The method according to [1], wherein the measuring of the hydrogen peroxide is performed using a hydrogen peroxide measuring reagent.

[3] The method according to [2], wherein the hydrogen peroxide measuring reagent is a reagent comprising peroxidase and a leuco chromogen.

[4] The method according to [3], wherein the leuco chromogen is a phenothiazine chromogen.

[5] The method according to [4], wherein the phenothiazine chromogen is 10-(carboxymethylaminocarbonyl)-3,7-bis(dimethylamino)phenothiazine.

[6] A reagent for measuring glycated hemoglobin in a hemoglobin-containing sample, comprising a proteolytic enzyme, fructosyl peptide oxidase, and at least one salt selected from the group consisting of a pyridinium salt represented by the following formula (I), a phosphonium salt represented by the following formula (II), an imidazolium salt represented by the following formula (III), and an isoquinolinium salt represented by the following formula (IV):

(I)

wherein $R^1$ represents a substituted or unsubstituted alkyl or a substituted or unsubstituted alkenyl; $R_a$ represents a hydrogen atom, a substituted or unsubstituted alkyl, or a substituted or unsubstituted alkenyl; n represents an integer of 1 to 5; and $X^-$ represents a monovalent anion;

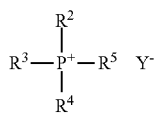
(II)

wherein $R^2$ to $R^5$ are the same or different, and each represents a substituted or unsubstituted alkyl; and $Y^-$ represents a monovalent anion;

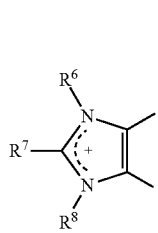
(III)

wherein $R^6$ and $R^8$ are the same or different, and each represents a substituted or unsubstituted alkyl or a substituted or unsubstituted alkenyl; $R^7$, $R^9$, and $R^{10}$ each represents a hydrogen atom, a substituted or unsubstituted alkyl, or a substituted or unsubstituted alkenyl; and Z⁻ represents a monovalent anion;

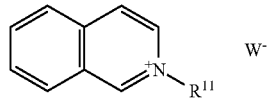

(IV)

wherein R¹¹ represents substituted or unsubstituted alkyl or substituted or unsubstituted alkenyl; and W⁻ represents a monovalent anion.

[7] The reagent according to [6], further comprising a hydrogen peroxide measuring reagent.

[8] The reagent according to [7], wherein the hydrogen peroxide measuring reagent is a reagent comprising peroxidase and a leuco chromogen.

[9] The reagent according to [8], wherein the leuco chromogen is a phenothiazine chromogen.

[10] The reagent according to [9], wherein the phenothiazine chromogen is 10-(carboxymethylaminocarbonyl)-3,7-bis(dimethylamino)phenothiazine.

[11] A kit for measuring glycated hemoglobin in a hemoglobin-containing sample comprising: a first reagent comprising a proteolytic enzyme and at least one salt selected from the group consisting of a pyridinium salt represented by the following formula (I), a phosphonium salt represented by the following formula (II), an imidazolium salt represented by the following formula (III), and an isoquinolinium salt represented by the following formula (IV); and a second reagent comprising fructosyl peptide oxidase:

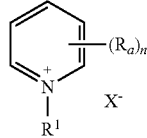

(I)

wherein R¹ represents a substituted or unsubstituted alkyl or a substituted or unsubstituted alkenyl; $R_a$ represents a hydrogen atom, a substituted or unsubstituted alkyl, or a substituted or unsubstituted alkenyl; n represents an integer of 1 to 5; and X⁻ represents a monovalent anion;

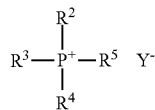

(II)

wherein R² to R⁵ are the same or different, and each represents a substituted or unsubstituted alkyl; and Y⁻ represents a monovalent anion;

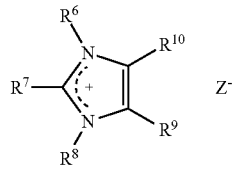

(III)

wherein R⁶ and R⁸ are the same or different, and each represents a substituted or unsubstituted alkyl or a substituted or unsubstituted alkenyl; R⁷, R⁹, and R¹⁰ each represents a hydrogen atom, a substituted or unsubstituted alkyl, or a substituted or unsubstituted alkenyl; and Z⁻ represents a monovalent anion;

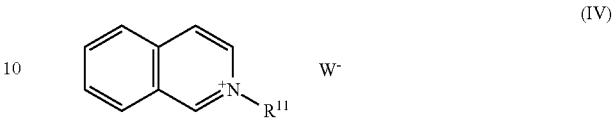

(IV)

wherein R¹¹ represents a substituted or unsubstituted alkyl or a substituted or unsubstituted alkenyl; and W⁻ represents a monovalent anion.

[12] The kit according to [11], wherein the first reagent and the second reagent or the second reagent and the first reagent further comprise peroxidase and a leuco chromogen, respectively.

[13] The kit according to [12], wherein the leuco chromogen is a phenothiazine chromogen.

[14] The kit according to [13], wherein the phenothiazine chromogen is 10-(carboxymethylaminocarbonyl)-3,7-bis(dimethylamino)phenothiazine.

[15] A method for preserving an aqueous solution containing a leuco chromogen, comprising adding at least one salt selected from the group consisting of a pyridinium salt represented by the following formula (I), a phosphonium salt represented by the following formula (II), an imidazolium salt represented by the following formula (III), and an isoquinolinium salt represented by the following formula (IV) to the aqueous solution containing a leuco chromogen:

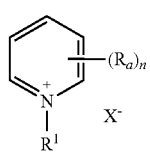

(I)

wherein R¹ represents a substituted or unsubstituted alkyl or a substituted or unsubstituted alkenyl; $R_a$ represents a hydrogen atom, a substituted or unsubstituted alkyl, or a substituted or unsubstituted alkenyl; n represents an integer of 1 to 5; and X⁻ represents a monovalent anion;

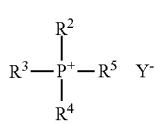

(II)

wherein R² to R⁵ are the same or different, and each represents a substituted or unsubstituted alkyl; and Y⁻ represents a monovalent anion;

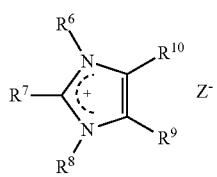

(III)

wherein R⁶ and R⁸ are the same or different, and each represents a substituted or unsubstituted alkyl or a substituted or unsubstituted alkenyl; R⁷, R⁹, and R¹⁰ each represents a hydrogen atom, a substituted or unsubstituted alkyl, or a substituted or unsubstituted alkenyl; and $Z^-$ represents a monovalent anion;

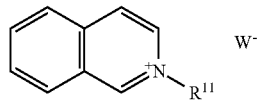

(IV)

wherein $R^{11}$ represents a substituted or unsubstituted alkyl or a substituted or unsubstituted alkenyl; and $W^-$ represents a monovalent anion.

[16] A method for stabilizing a leuco chromogen, comprising allowing the leuco chromogen to coexist in an aqueous solution comprising at least one salt selected from the group consisting of a pyridinium salt represented by the following formula (I), a phosphonium salt represented by the following formula (II), an imidazolium salt represented by the following formula (III), and an isoquinolinium salt represented by the following formula (IV):

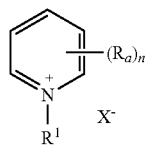

(I)

wherein $R^1$ represents a substituted or unsubstituted alkyl or a substituted or unsubstituted alkenyl; $R_a$ represents a hydrogen atom, a substituted or unsubstituted alkyl, or a substituted or unsubstituted alkenyl; n represents an integer of 1 to 5; and $X^-$ represents a monovalent anion,

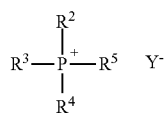

(II)

wherein $R^2$ to $R^5$ are the same or different, and each represents a substituted or unsubstituted alkyl; and $Y^-$ represents a monovalent anion;

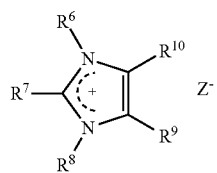

(III)

wherein $R^6$ and $R^8$ are the same or different, and each represents a substituted or unsubstituted alkyl or a substituted or unsubstituted alkenyl; $R^7$, $R^9$, and $R^{10}$ each represents a hydrogen atom, a substituted or unsubstituted alkyl, or a substituted or unsubstituted alkenyl; and $Z^-$ represents a monovalent anion;

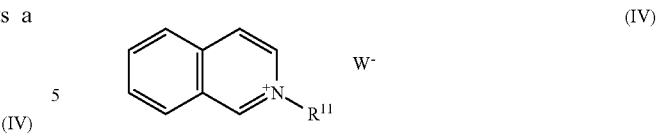

(IV)

wherein $R^{11}$ represents a substituted or unsubstituted alkyl or a substituted or unsubstituted alkenyl; and $W^-$ represents a monovalent anion.

[17] The method according to [15] or [16], wherein the leuco chromogen is a phenothiazine chromogen.
[18] The method according to [17], wherein the phenothiazine chromogen is 10-(carboxymethylaminocarbonyl)-3,7-bis (dimethylamino)phenothiazine.

Effect of the Invention

The present invention provides a method, a reagent, and a kit for accurately measuring glycated hemoglobin in a hemoglobin-containing sample, a method for preserving an aqueous solution containing a leuco chromogen and a method for stabilizing such a leuco chromogen that enable accurate measurement of glycated hemoglobin in a hemoglobin-containing sample.

Figure 1:
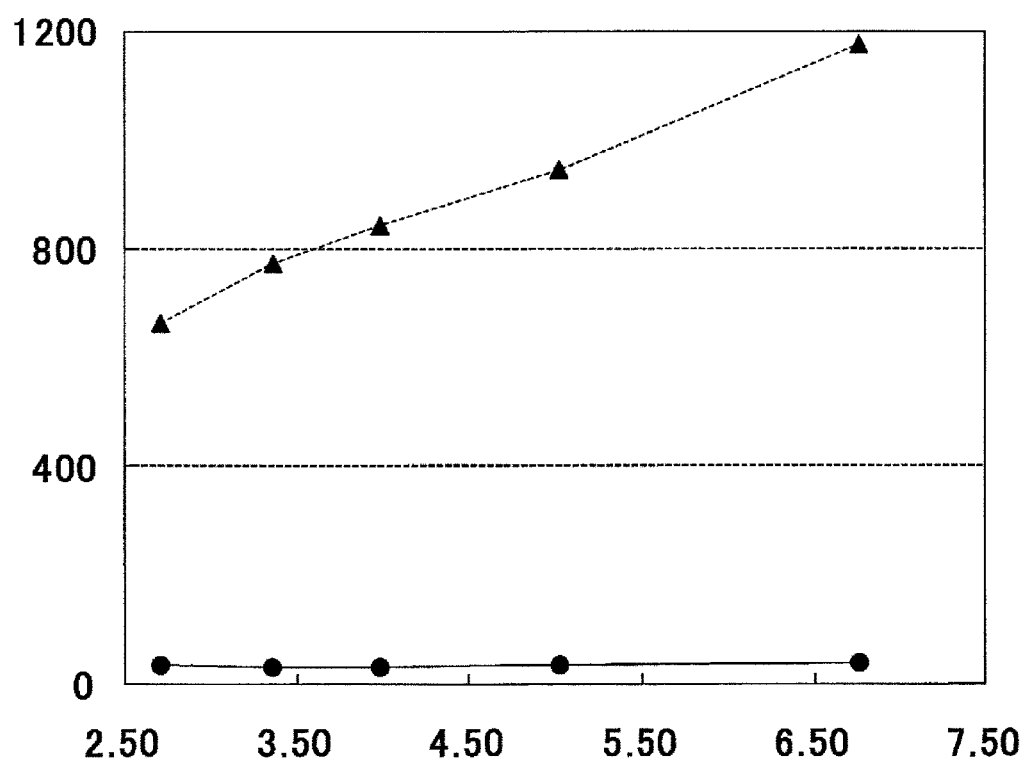
FIG. 1 is a graph showing the relationship between hemoglobin A1c (hereinafter, also referred to as HbA1c) concentration and reaction absorbance in the measurement of HbA1c in a sample using kits of Example 1 and Comparative Example 1. The symbol ▲ represents the results of measurement using the kit of Example 1. The symbol ● represents the results of measurement using the kit of Comparative Example 1. The ordinate represents reaction absorbance ($\times 10^{-4}$ Abs). The abscissa represents the theoretical concentration of HbA1c (μmol/L).

MODE FOR CARRYING OUT THE INVENTION (1) Method for Measuring Glycated Hemoglobin in Hemoglobin-Containing Sample The method for measuring glycated hemoglobin in a hemoglobin-containing sample according to the present invention comprises: reacting glycated hemoglobin in the hemoglobin-containing sample with a proteolytic enzyme in the presence of at least one salt selected from the group consisting of a pyridinium salt represented by the formula (I) described later, a phosphonium salt represented by the formula (II) described later, an imidazolium salt represented by the formula (III) described later, and an isoquinolinium salt represented by the formula (IV) described later; reacting the obtained reaction product with fructosyl peptide oxidase; and measuring the generated hydrogen peroxide.

Specifically, the measuring method comprises the following steps:
(1) reacting glycated hemoglobin in the hemoglobin-containing sample with a proteolytic enzyme in an aqueous medium comprising at least one salt selected from the group consisting of a pyridinium salt represented by the formula (I) described later, a phosphonium salt represented by the formula (II) described later, an imidazolium salt represented by the formula (III) described later, and an isoquinolinium salt represented by the formula (IV) described later;
(2) reacting the reaction product obtained in step (1) with fructosyl peptide oxidase to generate hydrogen peroxide;
(3) measuring the hydrogen peroxide generated in step (2); and
(4) correlating the amount of the hydrogen peroxide measured in step (3) to a calibration curve to determine the concentration of glycated hemoglobin in the hemoglobin-containing sample, the calibration curve representing the relationship between the amount of hydrogen peroxide and the concentration of glycated hemoglobin, prepared in advance using a known concentration of glycated hemoglobin.

The method for measuring glycated hemoglobin in a hemoglobin-containing sample according to the present invention also encompasses even a method involving calculating the ratio of the amount of glycated hemoglobin to the amount of total hemoglobin (i.e., total hemoglobin composed of hemoglobin plus glycated hemoglobin) in the hemoglobin-containing sample. In this case, a method for measuring glycated hemoglobin in a hemoglobin-containing sample according to the present invention specifically comprises the following steps:
(1) determining the amount of total hemoglobin (i.e., total hemoglobin composed of hemoglobin and glycated hemoglobin) in the hemoglobin-containing sample;
(2) reacting glycated hemoglobin in the hemoglobin-containing sample with a proteolytic enzyme in an aqueous medium comprising at least one salt selected from the group consisting of a pyridinium salt represented by the formula (I) described later, a phosphonium salt represented by the formula (II) described later, an imidazolium salt represented by the formula (III) described later, and an isoquinolinium salt represented by the formula (IV) described later;
(3) reacting the reaction product obtained in step (2) with fructosyl peptide oxidase to generate hydrogen peroxide;
(4) measuring the hydrogen peroxide generated in step (3);
(5) correlating the amount of the hydrogen peroxide measured in step (4) to a calibration curve to determine the amount of glycated hemoglobin in the hemoglobin-containing sample, the calibration curve representing the relationship between the amount of hydrogen peroxide and the amount of glycated hemoglobin, prepared in advance using a known amount of glycated hemoglobin; and
(6) calculating the ratio of the amount of glycated hemoglobin to the amount of total hemoglobin in the hemoglobin-containing sample from the amount of total hemoglobin determined in step (1) and the amount of glycated hemoglobin determined in step (5).

Step (1) of determining the amount of total hemoglobin can be performed after the following procedure: at least one salt selected from the group consisting of a pyridinium salt represented by the formula (I) described later, a phosphonium salt represented by the formula (II) described later, an imidazolium salt represented by the formula (III) described later, and an isoquinolinium salt represented by the formula (IV) described later is added to the hemoglobin-containing sample to denature hemoglobin and glycated hemoglobin in the hemoglobin-containing sample.

Alternatively, the determination of the amount of total hemoglobin in the hemoglobin-containing sample can be performed after the following procedure: a proteolytic enzyme and at least one salt selected from the group consisting of a pyridinium salt represented by the formula (I) described later, a phosphonium salt represented by the formula (II) described later, an imidazolium salt represented by the formula (III) described later, and an isoquinolinium salt represented by the formula (IV) described later are added to the hemoglobin-containing sample to degrade the denatured hemoglobin and glycated hemoglobin with the proteolytic enzyme.

The hemoglobin-containing sample used in the measuring method of the present invention is not particularly limited as long as the sample contains hemoglobin and is applicable to the method for measuring glycated hemoglobin according to the present invention. Examples thereof include whole blood, blood cells, mixed samples of blood cells and plasma, and hemolyzed samples of these samples. The hemolyzing treatment is not particularly limited as long as the treatment hemolyzes whole blood, blood cells, or mixed samples of blood cells and plasma. Examples thereof include physical, chemical, and biological methods. Examples of the physical method include a method using a hypotonic solution such as distilled water, and a method using sonic waves. Examples of the chemical method include a method using an organic solvent such as methanol, ethanol, or acetone, and a method using a polyoxyethylene surfactant. Examples of the biological method include a method using an antibody or a complement.

The glycated hemoglobin according to the present invention is generated through the binding of a sugar such as glucose to hemoglobin. Examples thereof include hemoglobin A1a, hemoglobin A1b, and hemoglobin A1c. Hemoglobin A1c is preferable.

In the present invention, a pyridinium salt represented by the following formula (I) [hereinafter, referred to as compound (I)] is used as the pyridinium salt:

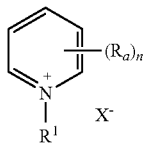
(I)

wherein $R^1$ represents substituted or unsubstituted alkyl or substituted or unsubstituted alkenyl; $R_a$ represents a hydrogen atom, substituted or unsubstituted alkyl, or substituted or unsubstituted alkenyl; n represents an integer of 1 to 5; and $X^-$ represents a monovalent anion.

Examples of alkyl in the substituted or unsubstituted alkyl represented by $R^1$ include linear alkyl having 1 to 20 carbon atoms, and branched alkyl having 3 to 20 carbon atoms. Linear alkyl having 8 to 20 carbon atoms, or branched alkyl having 8 to 20 carbon atoms is preferable. Examples of the linear alkyl having 1 to 20 carbon atoms include methyl, ethyl, propyl, butyl, pentyl, hexyl, heptyl, octyl, nonyl, decyl, undecyl, dodecyl (lauryl), tridecyl, tetradecyl (myristyl), pentadecyl, hexadecyl (cetyl), heptadecyl, octadecyl (stearyl), nonadecyl, and icosyl. Examples of the branched alkyl having 3 to 20 carbon atoms include isopropyl, isobutyl, isopentyl, isohexyl, isoheptyl, isooctyl, isononyl, isodecyl, isoundecyl, isododecyl, isotridecyl, isotetradecyl, isopentadecyl, isohexadecyl, isoheptadecyl, isooctadecyl, isononadecyl, isoicosyl, and octyldodecyl. Examples of the linear alkyl having 8 to 20 carbon atoms include octyl, nonyl, decyl, undecyl, dodecyl (lauryl), tridecyl, tetradecyl (myristyl), pentadecyl, hexadecyl (cetyl), heptadecyl, octadecyl (stearyl), nonadecyl, and icosyl. Examples of the branched alkyl having 8 to 20 carbon atoms include isooctyl, isononyl, isodecyl, isoundecyl, isododecyl, isotridecyl, isotetradecyl, isopentadecyl, isohexadecyl, isoheptadecyl, isooctadecyl, isononadecyl, isoicosyl, and octyldodecyl.

Examples of alkenyl in the substituted or unsubstituted alkenyl represented by $R^1$ include alkenyl having 2 to 20 carbon atoms. Alkenyl having 8 to 20 carbon atoms is preferable. Examples of the alkenyl having 2 to 20 carbon atoms include vinyl, propyl, allyl, butenyl, pentenyl, hexenyl, heptenyl, octenyl, nonenyl, decenyl, undecenyl, dodecenyl, tetradecenyl, pentadecenyl, hexadecenyl, heptadecenyl, octadecenyl, oleyl, nonadecenyl, and icosenyl. Examples of the alkenyl having 8 to 20 carbon atoms include octenyl, nonenyl, decenyl, undecenyl, dodecenyl, tetradecenyl, pentadecenyl, hexadecenyl, heptadecenyl, octadecenyl, oleyl, nonadecenyl, and icosenyl.

Examples of the substituent in the substituted alkyl or the substituted alkenyl represented by $R^1$ include a phenyl group, a hydroxy group, a sulfo group, a cyano group, and halogen atoms. Examples of the halogen atoms include chlorine, bromine, and iodine atoms.

Examples of alkyl in the substituted or unsubstituted alkyl represented by $R_a$ include linear alkyl having 1 to 20 carbon atoms, and branched alkyl having 3 to 20 carbon atoms. Examples of the linear alkyl having 1 to 20 carbon atoms include the aforementioned linear alkyl having 1 to 20 carbon atoms. Examples of the branched alkyl having 3 to 20 carbon atoms include the aforementioned branched alkyl having 3 to 20 carbon atoms.

Examples of alkenyl in the substituted or unsubstituted alkenyl represented by $R_a$ include alkenyl having 2 to 20 carbon atoms. Examples of the alkenyl having 2 to 20 carbon atoms include the aforementioned alkenyl having 2 to 20 carbon atoms.

Examples of the substituent in the substituted alkyl or the substituted alkenyl represented by $R_a$ include a phenyl group, a hydroxy group, a sulfo group, a cyano group, and halogen atoms. Examples of the phenyl group-substituted alkyl include benzyl and 1-phenylethyl. Examples of the halogen atoms include chlorine, bromine, and iodine atoms.

When the pyridine ring has two or more substituents, these substituents may be the same or different. $X^-$ in compound (I) represents a monovalent anion. Examples of the monovalent anion include anions such as halogen ions, $OH^-$, $PF_6^-$, $BF_4^-$, $CH_3CH_2OSO_3^-$, and $(CF_3SO_2)_2N^-$. Examples of the halogen ions include $Cl^-$, $Br^-$, and $I^-$.

Specific examples (products) of compound (I) include 1-dodecylpyridinium chloride (hereinafter, referred to as C12py; manufactured by Tokyo Chemical Industry Co., Ltd.), 1-cetylpyridinium chloride (hereinafter, referred to as C16py; manufactured by Tokyo Chemical Industry Co., Ltd.), 1-cetyl-4-methylpyridinium chloride (manufactured by Tokyo Chemical Industry Co., Ltd.), and N-octadecyl-4-stilbazole bromide (manufactured by Tokyo Chemical Industry Co., Ltd.).

In the method for measuring glycated hemoglobin according to the present invention, a concentration of compound (I) in the reaction solution is usually 0.0001 to 10%.

In the present invention, a phosphonium salt represented by the following formula (II) [hereinafter, referred to as compound (II)] is used as the phosphonium salt;

(II)

wherein $R^2$ to $R^5$ are the same or different and each represent substituted or unsubstituted alkyl; and $Y^-$ represents a monovalent anion.

Examples of alkyl in the substituted or unsubstituted alkyl represented by $R^2$ include linear alkyl having 8 to 20 carbon atoms, and branched alkyl having 8 to 20 carbon atoms. Examples of the linear alkyl having 8 to 20 carbon atoms include the aforementioned linear alkyl having 8 to 20 carbon atoms. Examples of the branched alkyl having 8 to 20 carbon atoms include the aforementioned branched alkyl having 8 to 20 carbon atoms. Examples of the substituent in the substituted alkyl include a phenyl group, a hydroxy group, a sulfo group, a cyano group, and halogen atoms. Examples of the phenyl group-substituted alkyl include benzyl and 1-phenylethyl. Examples of the halogen atoms include chlorine, bromine, and iodine atoms.

Examples of alkyl in the substituted or unsubstituted alkyl represented by each of $R^3$ to $R^5$ include linear alkyl having 1 to 20 carbon atoms, and branched alkyl having 3 to 20 carbon atoms. Examples of the linear alkyl having 1 to 20 carbon atoms include the aforementioned linear alkyl having 1 to 20 carbon atoms. Examples of the branched alkyl having 3 to 20 carbon atoms include the aforementioned branched alkyl having 3 to 20 carbon atoms. Examples of the substituent in the substituted alkyl include a phenyl group, a hydroxy group, a sulfo group, a cyano group, and halogen atoms. Examples of the phenyl group-substituted alkyl include benzyl and 1-phenylethyl. Examples of the halogen atoms include chlorine, bromine, and iodine atoms.

$Y^-$ represents a monovalent anion. Examples of the monovalent anion include anions such as halogen ions, $OH^-$, $PF_6^-$, $BF_4^-$, $CH_3CH_2OSO_3^-$, $(CF_3SO_2)_2N^-$, $B(C_6H_5)_4^-$, and benzotriazolate. Examples of the halogen ions include $Cl^-$, $Br^-$, and $I^-$.

Specific examples (products) of compound (II) include tetraoctylphosphonium bromide (manufactured by Tokyo Chemical Industry Co., Ltd.), tributyloctylphosphonium bromide (manufactured by Tokyo Chemical Industry Co., Ltd.), tributyldodecylphosphonium bromide (hereinafter, referred to as C12TBP; manufactured by Tokyo Chemical Industry Co., Ltd.), and tributylhexadecylphosphonium bromide (hereinafter, referred to as C16TBP; manufactured by Tokyo Chemical Industry Co., Ltd.).

In the method for measuring glycated hemoglobin according to the present invention, a concentration of compound (II) in the reaction solution is usually 0.0001 to 10%.

In the present invention, an imidazolium salt represented by the following formula (III) [hereinafter, referred to as compound (III)] is used as the imidazolium salt:

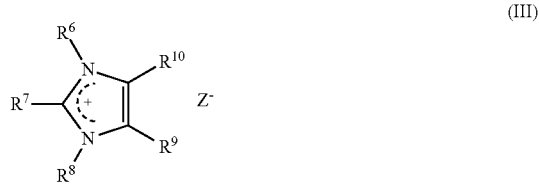

(III)

wherein $R^6$ and $R^8$ are the same or different and each represent substituted or unsubstituted alkyl or substituted or unsubstituted alkenyl; $R^7$, $R^9$, and $R^{10}$ each represent a hydrogen atom, substituted or unsubstituted alkyl, or substituted or unsubstituted alkenyl; and $Z^-$ represents a monovalent anion.

Examples of alkyl in the substituted or unsubstituted alkyl represented by $R^6$ include linear alkyl having 8 to 20 carbon atoms, and branched alkyl having 8 to 20 carbon atoms. Examples of the linear alkyl having 8 to 20 carbon atoms include the aforementioned linear alkyl having 8 to 20 carbon atoms. Examples of the branched alkyl having 8 to 20 carbon atoms include the aforementioned branched alkyl having 8 to 20 carbon atoms.

Examples of alkenyl in the substituted or unsubstituted alkenyl represented by $R^6$ include alkenyl having 8 to 20 carbon atoms. Examples of the alkenyl having 8 to 20 carbon atoms include the aforementioned alkenyl having 8 to 20 carbon atoms.

Examples of the substituent in the substituted alkyl or the substituted alkenyl represented by $R^6$ include a phenyl group, a hydroxy group, a sulfo group, a cyano group, and halogen atoms. Examples of the phenyl group-substituted alkyl include benzyl and 1-phenylethyl. Examples of the halogen atoms include chlorine, bromine, and iodine atoms.

Examples of alkyl in the substituted or unsubstituted alkyl represented by each of $R^7$, $R^8$, $R^9$, and $R^{10}$ include linear alkyl having 1 to 20 carbon atoms, and branched alkyl having 3 to 20 carbon atoms. Examples of the linear alkyl having 1 to 20 carbon atoms include the aforementioned linear alkyl having 1 to 20 carbon atoms. Examples of the branched alkyl having 3 to 20 carbon atoms include the aforementioned branched alkyl having 3 to 20 carbon atoms.

Examples of alkenyl in the substituted or unsubstituted alkenyl represented by each of $R^7$, $R^8$, $R^9$, and $R^{10}$ include alkenyl having 2 to 20 carbon atoms. Examples of the alkenyl having 2 to 20 carbon atoms include the aforementioned alkenyl having 2 to 20 carbon atoms.

Examples of the substituent in the substituted alkyl or the substituted alkenyl represented by each of $R^7$, $R^8$, $R^9$, and $R^{10}$ include a phenyl group, a hydroxy group, a sulfo group, a cyano group, and halogen atoms. Examples of the phenyl group-substituted alkyl include benzyl and 1-phenylethyl. Examples of the halogen atoms include chlorine, bromine, and iodine atoms.

$Z^-$ represents a monovalent anion. Examples of the monovalent anion include anions such as halogen ions, $OH^-$, $PF_6^-$, $BF_4^-$, $CH_3CH_2OSO_3^-$, $(CF_3SO_2)_2N^-$, $(CH_3O)_2P(=O)O^-$, $B(C_6H_5)_4^-$, $FeCl_4^-$, $CF_3BF_3^-$, $CF_3SO_3^-$, $(NC)_2N^-$, $CH_3(OCH_2CH_2)_2OSO_3^-$, $CH_3CH_2OSO_3^-$, $HSO_4^-$, and $4\text{-}CH_3C_6H_4SO_3^-$. Examples of the halogen ions include $Cl^-$, $Br^-$, and $I^-$.

Specific examples (products) of compound (III) include 1-methyl-3-octylimidazolium bromide (manufactured by Tokyo Chemical Industry Co., Ltd.), 1-methyl-3-octylimidazolium chloride (manufactured by Tokyo Chemical Industry Co., Ltd.), and 1-dodecyl-2-methyl-3-benzylimidazolium chloride (hereinafter, referred to as C12 MBI; manufactured by Wako Pure Chemical Industries, Ltd.).

In the measuring method of the present invention, a concentration of compound (III) in the reaction solution is usually 0.0001 to 10%.

In the present invention, an isoquinolinium salt represented by the following formula (IV) [hereinafter, referred to as compound (IV)] is used as the isoquinolinium salt:

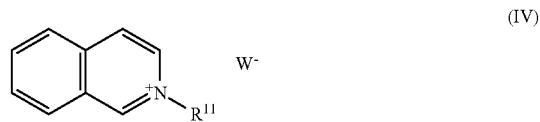

(IV)

wherein $R^{11}$ represents substituted or unsubstituted alkyl or substituted or unsubstituted alkenyl; and $W^-$ represents a monovalent anion.

Examples of alkyl in the substituted or unsubstituted alkyl represented by $R^{11}$ include linear alkyl having 8 to 20 carbon atoms, and branched alkyl having 8 to 20 carbon atoms. Examples of the linear alkyl having 8 to 20 carbon atoms include the aforementioned linear alkyl having 8 to 20 carbon atoms. Examples of the branched alkyl having 8 to 20 carbon atoms include the aforementioned branched alkyl having 8 to 20 carbon atoms.

Examples of alkenyl in the substituted or unsubstituted alkenyl represented by $R^{11}$ include alkenyl having 8 to 20 carbon atoms. Examples of the alkenyl having 8 to 20 carbon atoms include the aforementioned alkenyl having 8 to 20 carbon atoms.

Examples of the substituent in the substituted alkyl or the substituted alkenyl represented by $R^{11}$ include a phenyl group, a hydroxy group, a sulfo group, a cyano group, and halogen atoms. Examples of the phenyl group-substituted alkyl include benzyl and 1-phenylethyl. Examples of the halogen atoms include chlorine, bromine, and iodine atoms.

$W^-$ represents a monovalent anion. Examples of the monovalent anion include anions such as halogen ions. Examples of the halogen ions include $Cl^-$, $Br^-$, and $I^-$.

Specific examples (products) of compound (IV) include N-lauryl isoquinolinium chloride (manufactured by NOF Corp.) and N-lauryl isoquinolinium bromide (manufactured by NOF Corp.).

In the measuring method of the present invention, a concentration of compound (IV) in the reaction solution is usually 0.0001 to 10%.

The amount of total hemoglobin can be determined by applying a method known in the art, for example, cyanmethemoglobin method, oxyhemoglobin method, or SLS-hemoglobin method. The amount of total hemoglobin can be determined by using the cyanmethemoglobin method, the oxyhemoglobin method, the SLS-hemoglobin method, or the like not only to the hemoglobin-containing sample itself but to a hemoglobin-containing sample supplemented with at least one salt selected from the group consisting of compound (I), compound (II), compound (III), and compound (IV) or a hemoglobin-containing sample supplemented with at least one salt selected from the group consisting of compound (I), compound (II), compound (III), and compound (IV) and a proteolytic enzyme.

The reaction of glycated hemoglobin in the hemoglobin-containing sample with a proteolytic enzyme in an aqueous medium comprising at least one salt selected from the group consisting of compound (I), compound (II), compound (III), and compound (IV) can be performed under any condition as long as the proteolytic enzyme can act on glycated hemoglobin. The reaction of glycated hemoglobin in the hemoglobin-containing sample with a proteolytic enzyme is preferably performed in the aqueous medium. Examples of the aqueous medium include an aqueous medium described later. The reaction of glycated hemoglobin in the hemoglobin-containing sample with a proteolytic enzyme is performed usually at 10 to 50° C., preferably 20 to 40° C., and usually for 1 minute to 3 hours, preferably 2.5 minutes to 1 hour. The concentration of the proteolytic enzyme is not particularly limited as long as the reaction of glycated hemoglobin in the hemoglobin-containing sample with the proteolytic enzyme proceeds. The concentration is usually 50 to 25000 kU/L, preferably 250 to 10000 kU/L.

The proteolytic enzyme is not particularly limited as long as the enzyme is reactive to glycated hemoglobin in the hemoglobin-containing sample to generate a glycated peptide from the glycated hemoglobin. Examples thereof include serine protease (chymotrypsin, subtilisin, etc.), cysteine protease (papain, caspase, etc.), aspartic acid protease (pepsin, cathepsin D, etc.), metalloprotease (thermolysin, etc.), N-terminal threonine protease, and glutamic acid protease. In the present invention, a commercially available proteolytic enzyme can be used. Examples of the commercially available product include Protease P "Amano" 3G and Protease K "Amano" (both manufactured by Amano Enzyme Inc.), Actinase AS and Actinase E (both manufactured by Kaken Pharma Co., Ltd.), Thermolysin (manufactured by Daiwa Fine Chemicals Co., Ltd.), and Sumizyme MP (manufactured by Shin Nihon Chemical Co., Ltd.).

The reaction of glycated hemoglobin in the hemoglobin-containing sample with the proteolytic enzyme affords a reaction product comprising a glycated peptide. Subsequently, this glycated peptide in the reaction product reacts with fructosyl peptide oxidase to generate hydrogen peroxide. The reaction of the glycated peptide with fructosyl peptide oxidase is preferably performed in an aqueous medium. Examples of the aqueous medium include an aqueous medium described later. The reaction of the glycated peptide with fructosyl peptide oxidase is performed usually at 10 to 50° C., preferably 20 to 40° C., and usually for 1 minute to 3 hours, preferably 2.5 minutes to hour. The concentration of the fructosyl peptide oxidase is not particularly limited as long as the reaction of the glycated hemoglobin with the fructosyl peptide oxidase proceeds, and is usually 0.1 to 30 kU/L, preferably 0.2 to 15 kU/L.

The fructosyl peptide oxidase used in the present invention is not particularly limited as long as the enzyme is reactive to the glycated peptide to generate hydrogen peroxide. Examples thereof include fructosyl peptide oxidases derived from filamentous bacteria, yeasts, actinomycetes, bacteria, or archaebacteria. In the present invention, commercially available fructosyl peptide oxidase can be used. Examples of the commercially available product include FPOX-CE (manufactured by Kikkoman Corp.), FPOX-EE (manufactured by Kikkoman Corp.), and FPOX-CET (manufactured by Kikkoman Corp.).

The method for measuring the generated hydrogen peroxide is not particularly limited as long as the method is capable of measuring hydrogen peroxide. Examples thereof include a method using an electrode, and a method using a hydrogen peroxide measuring reagent. A method using a hydrogen peroxide measuring reagent is preferable. The hydrogen peroxide measuring reagent refers to a reagent for converting hydrogen peroxide to a detectable substance. Examples of the detectable substance include dyes, light (luminescence), and fluorescence. A dye is preferable.

In case the detectable substance is a dye, examples of the hydrogen peroxide measuring reagent include a reagent comprising a peroxidatively active substance such as peroxidase and a chromogen capable of developing color by oxidation. Examples of the chromogen capable of developing color by oxidation include oxidative coupling-type chromogens and leuco chromogens. A leuco chromogen is preferable. Examples of the leuco chromogen include phenothiazine chromogens, triphenylmethane chromogens, diphenylamine chromogens, o-phenylenediamine, hydroxypropionic acid, diaminobenzidine, and tetramethylbenzidine. A phenothiazine chromogen is preferable. Examples of the phenothiazine chromogen include 10-N-carboxymethylcarbamoyl-3,7-bis(dimethylamino)-10H-phenothiazine (CCAP), 10-N-methylcarbamoyl-3,7-bis(dimethylamino)-10H-phenothiazine (MCDP), and 10-N-(carboxymethylaminocarbonyl)-3,7-bis(dimethylamino)-10H-phenothiazine sodium salt (DA-67). Among these phenothiazine chromogens, 10-N-(carboxymethylaminocarbonyl)-3,7-bis(dimethylamino)-10H-phenothiazine sodium salt (DA-67) is particularly preferable. Examples of the triphenylmethane chromogens include N,N,N',N',N",N"-hexa(3-sulfopropyl)-4,4',4"-triaminotriphenylmethane (TPM-PS). Examples of the diphenylamine chromogens include N-(carboxymethylaminocarbonyl)-4,4'-bis(dimethylamino)diphenylamine sodium salt (DA-64), 4,4'- bis(dimethylamino)diphenylamine, and bis[3-bis(4-chlorophenyl)methyl-4-dimethylaminophenyl]amine (BCMA).

In case the detectable substance is light (luminescence), examples of the hydrogen peroxide measuring reagent include a reagent comprising a peroxidatively active substance such as peroxidase and a chemiluminescent material. Examples of the chemiluminescent substance include luminol, isoluminol, lucigenin, and acridinium ester.

In case the detectable substance is fluorescence, examples of the hydrogen peroxide measuring reagent include a reagent comprising a peroxidatively active substance such as peroxidase and a fluorescent substance. Examples of the fluorescent substance include 4-hydroxyphenylacetic acid, 3-(4-hydroxyphenyl)propionic acid, and coumarin.

(2) Reagent for Measuring Glycated Hemoglobin in Hemoglobin-Containing Sample

The reagent for measuring glycated hemoglobin in a hemoglobin-containing sample according to the present invention comprises a proteolytic enzyme, fructosyl peptide oxidase, and at least one salt selected from the group consisting of compound (I), compound (II), compound (III), and compound (IV). The measuring reagent of the present invention is used in the method for measuring glycated hemoglobin in a hemoglobin-containing sample according to the present invention. The measuring reagent of the present invention may further comprise a hydrogen peroxide measuring reagent.

Examples of the proteolytic enzyme, the fructosyl peptide oxidase, compound (I), compound (II), compound (III), compound (IV), and the hydrogen peroxide measuring reagent in the measuring reagent of the present invention include the aforementioned proteolytic enzyme, the fructosyl peptide oxidase, compound (I), compound (II), compound (III), compound (IV), and the hydrogen peroxide measuring reagent, respectively.

A concentration of the proteolytic enzyme in the measuring reagent of the present invention is usually 50 to 25000 kU/L, preferably 250 to 10000 kU/L. A concentration of the fructosyl peptide oxidase in the measuring reagent of the present invention is usually 0.1 to 30 kU/L, preferably 0.2 to 15 kU/L.

A concentration of Compound (I) in the measuring reagent of the present invention is usually 0.0001 to 10%. A concentration of Compound (II) in the measuring reagent of the present invention is usually 0.0001 to 10%. A concentration of the Compound (III) in the measuring reagent of the present invention is usually 0.0001 to 10%. A concentration of Compound (IV) in the measuring reagent of the present invention is usually 0.0001 to 10%.

The measuring reagent of the present invention can optionally comprise an aqueous medium, a stabilizer, an antiseptic, salts, an interference inhibitor, an organic solvent, and the like.

Examples of the aqueous medium include deionized water, distilled water, and buffer solutions. A buffer solution is preferable.

The pH of the aqueous medium is not particularly limited as long as the method for measuring glycated hemoglobin can be carried out using the reagent for measuring glycated hemoglobin according to the present invention. The pH is, for example, 4 to 10. In the case of using a buffer solution as the aqueous medium, a buffer is preferably used according to the set pH. Examples of the buffer used in the buffer solution include a tris(hydroxymethyl)aminomethane buffer, a phosphate buffer, a borate buffer, and Good's buffers.

Examples of the Good's buffers include 2-morpholinoethanesulfonic acid (MES), bis(2-hydroxyethyl)iminotris(hydroxymethyl)methane (Bis-Tris), N-(2-acetamido)iminodiacetic acid (ADA), piperazine-N,N'-bis(2-ethanesulfonic acid) (PIPES), N-(2-acetamido)-2-aminoethanesulfonic acid (ACES), 3-morpholino-2-hydroxypropanesulfonic acid (MOPSO), N,N-bis(2-hydroxyethyl)-2-aminoethanesulfonic acid (BES), 3-morpholinopropanesulfonic acid (MOPS), N-[tris(hydroxymethyl)methyl]-2-aminoethanesulfonic acid (TES), 2-[4-(2-hydroxyethyl)-1-piperazinyl]ethanesulfonic acid (HEPES), 3-[N,N-bis(2-hydroxyethyl)amino]-2-hydroxypropanesulfonic acid (DIPSO), N-[tris(hydroxymethyl)methyl]-2-hydroxy-3-aminopropanesulfonic acid (TAPSO), piperazine-N,N'-bis(2-hydroxypropanesulfonic acid) (POPSO), 3-[4-(2-hydroxyethyl)-1-piperazinyl]-2-hydroxypropanesulfonic acid (HEPPSO), 3-[4-(2-hydroxyethyl)-1-piperazinyl]propanesulfonic acid [(H)EPPS], N-[tris(hydroxymethyl)methyl]glycine (Tricine), N,N-bis(2-hydroxyethyl)glycine (Bicine), N-tris(hydroxymethyl)methyl-3-aminopropanesulfonic acid (TAPS), N-cyclohexyl-2-aminoethanesulfonic acid (CHES), N-cyclohexyl-3-amino-2-hydroxypropanesulfonic acid (CAPSO), and N-cyclohexyl-3-aminopropanesulfonic acid (CAPS).

A concentration of the buffer solution is usually 0.001 to 2.0 mol/L, preferably 0.005 to 1.0 mol/L.

Examples of the stabilizer include ethylenediaminetetraacetic acid (EDTA), sucrose, calcium chloride, calcium acetate, calcium nitrate, potassium ferrocyanide, bovine serum albumin (BSA), and polyoxyethylene surfactants such as polyoxyethylene alkylphenyl ether. Examples of the antiseptic include sodium azide and antibiotics. Examples of the salts include sodium chloride, sodium nitrate, sodium sulfate, sodium carbonate, sodium formate, sodium acetate, potassium chloride, potassium nitrate, potassium sulfate, potassium carbonate, potassium formate, and potassium acetate. Examples of the interference inhibitor include ascorbic acid oxidase for eliminating the influence of ascorbic acid. Examples of the organic solvent include solubilizers that make the leuco chromogen soluble in the aqueous medium, such as dimethylformamide (DMF), dimethyl sulfoxide (DMSO), dioxane, acetone, methanol, and ethanol.

(3) Kit for Measuring Glycated Hemoglobin in Hemoglobin-Containing Sample

The reagent for measuring glycated hemoglobin in a hemoglobin-containing sample according to the present invention can be preserved, distributed, and used in the form of a kit. The kit for measuring glycated hemoglobin in a hemoglobin-containing sample according to the present invention is used in the method for measuring glycated hemoglobin in a hemoglobin-containing sample according to the present invention. Examples of the measuring kit of the present invention include 2-reagent kits and 3-reagent kits. A 2-reagent kit is preferable.

The kit for measuring glycated hemoglobin in a hemoglobin-containing sample according to the present invention is not particularly limited as long as the kit enables the method for measuring glycated hemoglobin in a hemoglobin-containing sample according to the present invention. Examples of the 2-reagent kit include: a kit comprising a first reagent comprising a proteolytic enzyme and at least one salt selected from the group consisting of compound (I), compound (II), compound (III), and compound (IV), and a second reagent comprising fructosyl peptide oxidase; and a kit comprising a first reagent comprising a proteolytic enzyme and at least one salt selected from the group consisting of compound (I), compound (II), compound (III), and compound (IV), and a second reagent comprising fructosyl peptide oxidase, wherein either the first reagent or the second reagent, or both comprise a hydrogen peroxide measuring reagent. In the case of using a hydrogen peroxide measuring reagent comprising peroxidase and a leuco chromogen, the peroxidase and the leuco chromogen are preferably contained in separate reagents. Specifically, the peroxidase and the leuco chromogen are preferably contained in the first reagent and the second reagent or the second reagent and the first reagent, respectively.

A concentration of the proteolytic enzyme in the measuring kit of the present invention is usually 100 to 30000 kU/L, preferably 500 to 10000 kU/L. A concentration of the fructosyl peptide oxidase in the measuring kit of the present invention is usually 0.5 to 100 kU/L, preferably 1 to 50 kU/L.

A concentration of Compound (I) in the reagent constituting the measuring kit of the present invention is usually 0.0001 to 10%. A concentration of Compound (II) in the measuring kit of the present invention is usually 0.0001 to 10%. A concentration of Compound (III) in the measuring kit of the present invention is usually 0.0001 to 10%. A concentration of the Compound (IV) in the measuring kit of the present invention is usually 0.0001 to 10%.

(4) Method for Preserving Aqueous Solution Containing Leuco Chromogen and Method for Stabilizing Leuco Chromogen The present invention also relates to a method for preserving an aqueous solution containing a leuco chromogen. According to the method for preserving an aqueous solution containing a leuco chromogen according to the present invention, a leuco chromogen is stably preserved in an aqueous solution. In the present invention, the phrase "leuco chromogen is stably preserved in an aqueous solution" means that the leuco chromogen in the aqueous solution is stable against heat or stable against light, preferably, stable against heat and light. In the method for preserving an aqueous solution containing a leuco chromogen according to the present invention, at least one salt selected from the group consisting of compound (I), compound (II), compound (III), and compound (IV) is added to the aqueous solution containing a leuco chromogen. Examples of compound (I), compound (II), compound (III), and compound (IV) include aforementioned compound (I), compound (II), compound (III), and compound (IV).

In the method for preserving an aqueous solution containing a leuco chromogen according to the present invention, a concentration of compound (I), compound (II), compound (III), or compound (IV) is usually 0.0001 to 10%, preferably 0.0005 to 5%.

In the method for preserving a leuco chromogen according to the present invention, the preservation stability of the leuco chromogen can be evaluated on the basis of the coloring of the aqueous solution containing this leuco chromogen. It can be evaluated that stronger the coloring, i.e., larger the absorbance of the aqueous solution containing a leuco chromogen, the stability of leuco chromogen in the solution is worse. By contrast, it can be evaluated that weaker the coloring, i.e., smaller the absorbance of the aqueous solution containing a leuco chromogen, the stability of leuco chromogen in the solution is better.

The aqueous solution containing a leuco chromogen according to the present invention refers to an aqueous solution containing a leuco chromogen dissolved in an aqueous medium and can be prepared by adding and dissolving the leuco chromogen in the aqueous medium. The aqueous medium in which the leuco chromogen is dissolved is not particularly limited as long as the aqueous medium is capable of dissolving therein the leuco chromogen. Examples thereof include deionized water, distilled water, and buffer solution. A buffer solution is preferable. For the preparation of the aqueous solution containing a leuco chromogen, an organic solvent can be used as a solubilizer that makes the leuco chromogen soluble in the aqueous medium. The leuco chromogen dissolved in the organic solvent can be added to the aqueous medium and dissolved in this aqueous medium to prepare the aqueous solution containing the leuco chromogen. The organic solvent is not particularly limited as long as the organic solvent is capable of dissolving therein the leuco chromogen. Examples thereof include dimethylformamide (DMF), dimethyl sulfoxide (DMSO), dioxane, acetone, methanol, and ethanol.

The pH of the aqueous medium is not particularly limited as long as the leuco chromogen is dissolved. The pH is, for example, 4 to 10. In the case of using a buffer solution as the aqueous medium, a buffer is preferably used according to the set pH. Examples of the buffer used in the buffer solution include the aforementioned buffer.

The concentration of the buffer solution is not particularly limited as long as the leuco chromogen is dissolved, and is usually 0.001 to 2.0 mol/L, preferably 0.005 to 1.0 mol/L.

Examples of the leuco chromogen according to the present invention include the aforementioned leuco chromogen.

The present invention further relates to a method for stabilizing a leuco chromogen. The stabilization of a leuco chromogen according to the present invention means that the leuco chromogen in an aqueous solution containing this leuco chromogen is stabilized against heat or stabilized against light, preferably stabilized against heat and light. In this context, the stabilization of the leuco chromogen can be evaluated on the basis of the coloring of the aqueous solution containing this leuco chromogen. It can be evaluated that stronger the coloring, i.e., larger the absorbance of the aqueous solution containing a leuco chromogen, the stability of leuco chromogen in the solution is worse. By contrast, it can be evaluated that weaker the coloring, i.e., smaller the absorbance of the aqueous solution containing a leuco chromogen, the stability of leuco chromogen in the solution is better.

In the method for stabilizing a leuco chromogen according to the present invention, the leuco chromogen is allowed to coexist in an aqueous solution comprising at least one salt selected from the group consisting of compound (I), compound (II), compound (III), and compound (IV). Examples of compound (I), compound (II), compound (III), and compound (IV) used in the method for stabilizing a leuco chromogen according to the present invention include aforementioned compound (I), compound (II), compound (III), and compound (IV).

Examples of the leuco chromogen and the aqueous solution containing a leuco chromogen, used in the stabilization method of the present invention include the aforementioned leuco chromogen and the aqueous solution containing a leuco chromogen, respectively, in the method for preserving a leuco chromogen. In the present invention, the concentration of the leuco chromogen in the aqueous solution containing the leuco chromogen is not particularly limited as long as the leuco chromogen is dissolved in the aqueous medium, and is usually 0.0001 to 2.0 mmol/L, preferably 0.0005 to 1.0 mmol/L.

In the present invention, compound (I), a concentration of compound (II), compound (III), or compound (IV) coexisting with the leuco chromogen in the aqueous solution is usually 0.0001 to 10%, preferably 0.0005 to 5%.

In the present invention, the method for determining the stability against heat of the leuco chromogen is not particularly limited as long as the method is capable of determining the stability of the leuco chromogen against heat. Examples thereof include a method involving storing the aqueous solution containing the leuco chromogen at 5° C. or 30° C. and then determining the coloring of the aqueous solution using an absorption spectrometer.

Also, in the present invention, the method for determining the stability against light of the leuco chromogen is not particularly limited as long as the method is capable of determining the stability of the leuco chromogen against light. Examples thereof include a method involving irradiating the aqueous solution containing the leuco chromogen with light for 15 hours and then determining the coloring of the aqueous solution thus irradiated using an absorption spectrometer.

Hereinafter, the present invention will be described in more detail with reference to Examples. However, the scope of the present invention is not limited to these examples by any means.

In Examples, Comparative Examples, and Test Examples below, reagents and enzymes from the following manufacturers were used.

Bis-Tris (manufactured by Dojindo Laboratories), ADA (manufactured by Dojindo Laboratories), MES (manufactured by Dojindo Laboratories), calcium acetate monohydrate (manufactured by Kanto Chemical Co., Inc.), calcium chloride dihydrate (manufactured by Wako Pure Chemical Industries, Ltd.), DA-67 (manufactured by Wako Pure Chemical Industries, Ltd.), 1-dodecylpyridinium chloride (C12py) (pyridinium salt; manufactured by Tokyo Chemical Industry Co., Ltd.), 1-cetylpyridinium chloride (C16py) (pyridinium salt; manufactured by Tokyo Chemical Industry Co., Ltd.), dodecyltributylphosphonium chloride (C12TBP) (phosphonium salt; manufactured by Tokyo Chemical Industry Co., Ltd.), hexadecyltributylphosphonium chloride (C16TBP) (phosphonium salt; manufactured by Tokyo Chemical Industry Co., Ltd.), 1-dodecyl-2-methyl-3-benzylimidazolium chloride (C12 MBI) (imidazolium salt; manufactured by Wako Pure Chemical Industries, Ltd.), N-lauryl isoquinolinium chloride (Firet Q) (isoquinolinium salt; manufactured by NOF Corp.), Thermolysin (proteolytic enzyme; manufactured by Daiwa Fine Chemicals Co., Ltd.), Actinase AS (proteolytic enzyme; manufactured by Kaken Pharma Co., Ltd.), FPOX-CE (fructosyl peptide oxidase; manufactured by Kikkoman Corp.), and peroxidase (manufactured by Toyobo Co., Ltd.).

Example 1

A kit for HbA1c measurement consisting of the following first and second reagents was prepared.

| First reagent | |
|---|---|
| Bis-Tris (pH 6.0) | 10 mmol/L |
| C12py | 2.0 g/L |
| Calcium acetate monohydrate | 10 mmol/L |
| Thermolysin | 1200 kU/L |
| DA-67 | 20 μmol/L |
| Second reagent | |
| ADA (pH 7.0) | 50 mmol/L |
| FPOX-CE | 12 kU/L |
| Peroxidase | 120 kU/L |

Example 2

A kit for HbA1c measurement consisting of the following first and second reagents was prepared.

| First reagent | |
|---|---|
| Bis-Tris (pH 6.0) | 10 mmol/L |
| C16py | 0.35 g/L |
| Calcium acetate monohydrate | 10 mmol/L |
| Thermolysin | 1200 kU/L |
| DA-67 | 20 μmol/L |
| Second reagent | |
| ADA (pH 7.0) | 50 mmol/L |
| FPOX-CE | 12 kU/L |
| Peroxidase | 120 kU/L |

Example 3

A kit for HbA1c measurement consisting of the following first and second reagents was prepared.

| First reagent | |
|---|---|
| Bis-Tris (pH 6.0) | 10 mmol/L |
| C12TBP | 0.8 g/L |
| Calcium acetate monohydrate | 10 mmol/L |
| Thermolysin | 1200 kU/L |
| DA-67 | 20 μmol/L |
| Second reagent | |
| ADA (pH 7.0) | 50 mmol/L |
| FPOX-CE | 12 kU/L |
| Peroxidase | 120 kU/L |

Example 4

A kit for HbA1c measurement consisting of the following first and second reagents was prepared.

| First reagent | |
|---|---|
| Bis-Tris (pH 6.0) | 10 mmol/L |
| C16TBP | 0.2 g/L |
| Calcium acetate monohydrate | 10 mmol/L |
| Thermolysin | 1200 kU/L |
| DA-67 | 20 μmol/L |
| Second reagent | |
| ADA (pH 7.0) | 50 mmol/L |
| FPOX-CE | 12 kU/L |
| Peroxidase | 120 kU/L |

Example 5

A kit for HbA1c measurement consisting of the following first and second reagents was prepared.

| First reagent | |
|---|---|
| Bis-Tris (pH 6.0) | 10 mmol/L |
| C12MBI | 0.5 g/L |
| Calcium acetate monohydrate | 10 mmol/L |
| Thermolysin | 1200 kU/L |
| DA-67 | 20 μmol/L |
| Second reagent | |
| ADA (pH 7.0) | 50 mmol/L |
| FPOX-CE | 12 kU/L |
| Peroxidase | 120 kU/L |

Example 6

A kit for HbA1c measurement consisting of the following first and second reagents was prepared.

| First reagent | |
|---|---|
| Bis-Tris (pH 6.0) | 10 mmol/L |
| Firet Q | 0.5 g/L |
| Calcium acetate monohydrate | 10 mmol/L |
| Thermolysin | 1200 kU/L |
| DA-67 | 20 µmol/L |
| Second reagent | |
| ADA (pH 7.0) | 50 mmol/L |
| FPOX-CE | 12 kU/L |
| Peroxidase | 120 kU/L |

Comparative Example 1

A kit for HbA1c measurement consisting of the following first and second reagents was prepared.

| First reagent | |
|---|---|
| Bis-Tris (pH 6.0) | 10 mmol/L |
| Calcium acetate monohydrate | 10 mmol/L |
| Thermolysin | 1200 kU/L |
| DA-67 | 20 µmol/L |
| Second reagent | |
| ADA (pH 7.0) | 50 mmol/L |
| FPOX-CE | 12 kU/L |
| Peroxidase | 120 kU/L |

Example 7

The kit of Example 1 was used as a kit for HbA1c measurement. Blood cells obtained by the centrifugation of human blood were hemolyzed by dilution with deionized water to prepare samples. Hemolyzed samples with an HbA1c concentration valued at 2.7 µmol/L, 3.4 µmol/L, 4.0 µmol/L, 5.0 µmol/L, or 6.8 µmol/L by the KO500 method, which is a standard HbA1c measurement, and the SLS-hemoglobin method, which is one of hemoglobin measurements, were used to determine the reaction absorbance for each sample by the following procedures:

9.6 µL of each sample and 120 µL of the first reagent of the kit of Example 1 were added to a reaction cuvette and incubated at 37° C. for 5 minutes (first reaction). The absorbance (E1) of the reaction solution was determined at a primary wavelength of 660 nm and a secondary wavelength of 800 nm. Subsequently, 40 µL of the second reagent was added to this reaction solution, and the mixture was further incubated at 37° C. for 5 minutes (second reaction). The absorbance (E2) of the reaction solution was determined at a primary wavelength of 660 nm and a secondary wavelength of 800 nm. E1 was subtracted from E2 to calculate an absorbance difference $\Delta E$. The relationship between HbA1c concentration and $\Delta E$ is shown as to each sample in FIG. 1.

Comparative Example 2

The reaction absorbance for each sample was calculated in the same way as in Example 7 except that the kit of Comparative Example 1 was used instead of the kit of Example 1 used in Example 7.

As shown in FIG. 1, no quantitative relationship was found between HbA1c concentration and reaction absorbance for the kit of Comparative Example 1 free from C12py, whereas the quantitative relationship was found between HbA1c concentration and reaction absorbance for the kit of Example 1 comprising C12py. It proved that use of the kit of Example 1 enabled measurement of HbA1c in a sample.

Example 8

The reaction absorbance for each sample was calculated in the same way as in Example 7 except that the kit of Example 2 was used instead of the kit of Example 1 used in Example 7. The relationship between HbA1c concentration and $\Delta E$ is shown as to each sample in FIG. 2.

Figure 2:
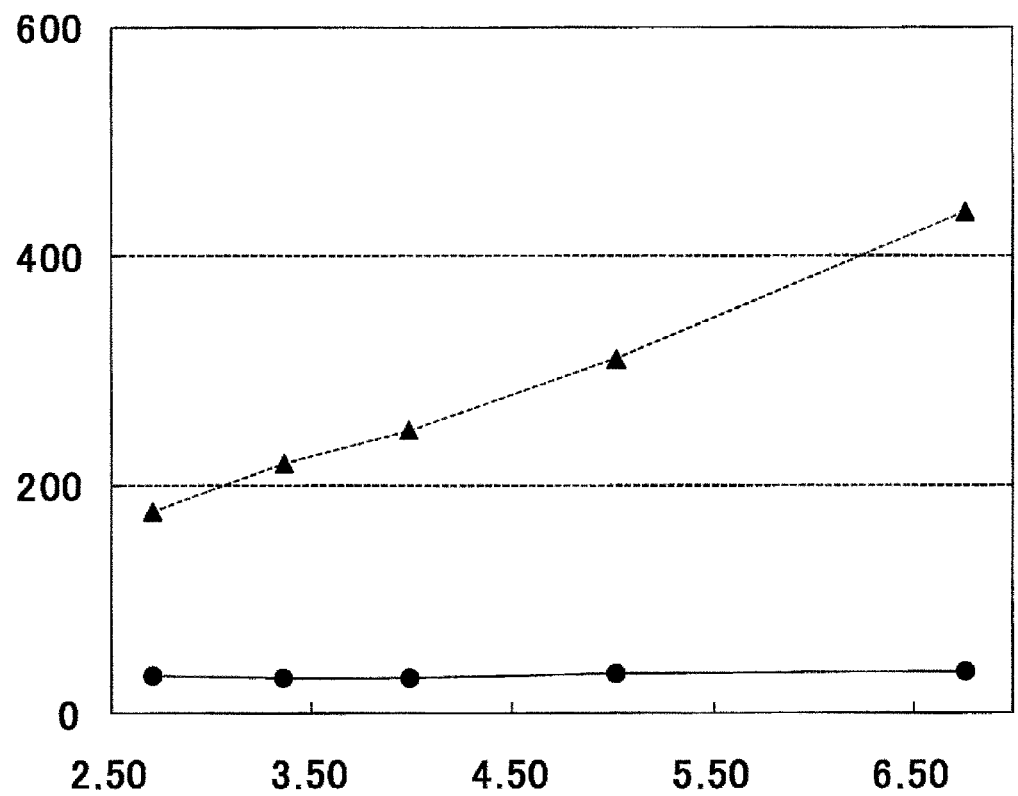
FIG. 2 is a graph showing the relationship between HbA1c concentration and reaction absorbance in the measurement of HbA1c in a sample using kits of Example 2 and Comparative Example 1. The symbol ▲ represents the results of measurement using the kit of Example 2. The symbol ● represents the results of measurement using the kit of Comparative Example 1. The ordinate represents reaction absorbance ($\times 10^{-4}$ Abs). The abscissa represents the theoretical concentration of HbA1c (μmol/L).

As shown in FIG. 2, no quantitative relationship was found between HbA1c concentration and reaction absorbance for the kit of Comparative Example 1 free from C16py, whereas the quantitative relationship was found between HbA1c concentration and reaction absorbance for the kit of Example 2 comprising C16py. It proved that use of the kit of Example 2 enabled measurement of HbA1c in a sample.

Example 9

The reaction absorbance for each sample was calculated in the same way as in Example 7 except that the kit of Example 3 was used instead of the kit of Example 1 used in Example 7. The relationship between HbA1c concentration and $\Delta E$ is shown as to each sample in FIG. 3.

Figure 3:
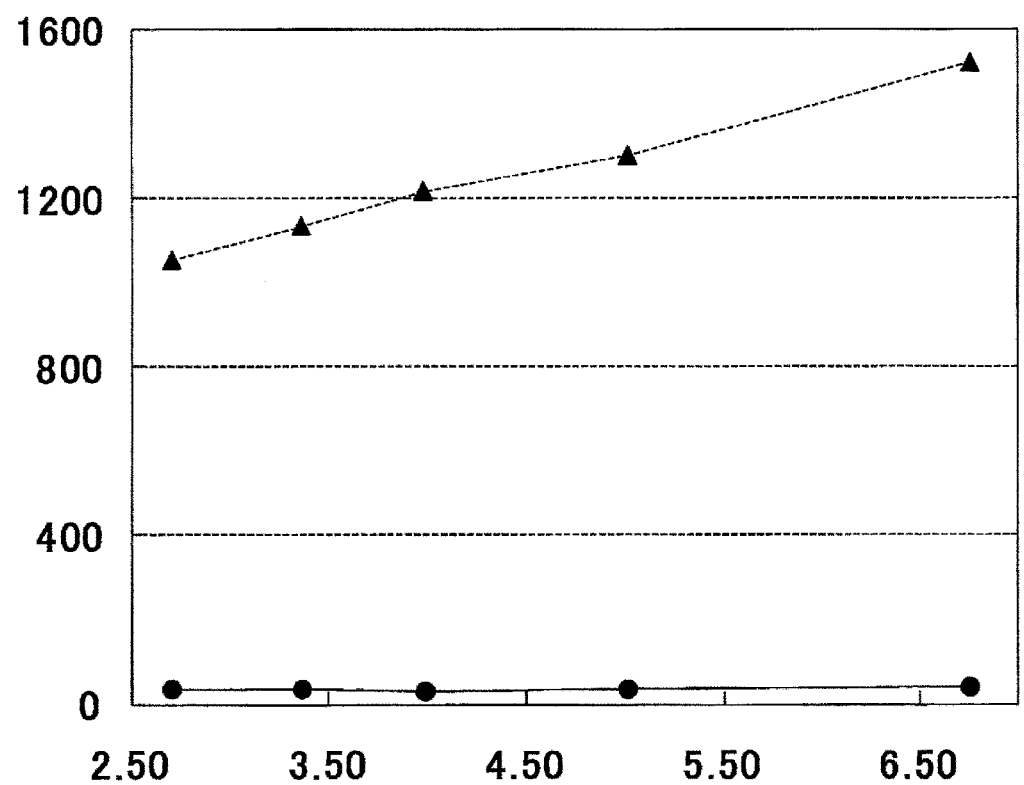
FIG. 3 is a graph showing the relationship between HbA1c concentration and reaction absorbance in the measurement of HbA1c in a sample using kits of Example 3 and Comparative Example 1. The symbol ▲ represents the results of measurement using the kit of Example 3. The symbol ● represents the results of measurement using the kit of Comparative Example 1. The ordinate represents reaction absorbance ($\times 10^{-4}$ Abs). The abscissa represents the theoretical concentration of HbA1c (μmol/L).

As shown in FIG. 3, no quantitative relationship was found between HbA1c concentration and reaction absorbance for the kit of Comparative Example 1 free from C12TBP, whereas the quantitative relationship was found between HbA1c concentration and reaction absorbance for the kit of Example 3 comprising C12TBP. It proved that use of the kit of Example 3 enabled measurement of HbA1c in a sample.

Example 10

The reaction absorbance for each sample was calculated in the same way as in Example 7 except that the kit of Example 4 was used instead of the kit of Example 1 used in Example 7. The relationship between HbA1c concentration and $\Delta E$ is shown as to each sample in FIG. 4.

Figure 4:
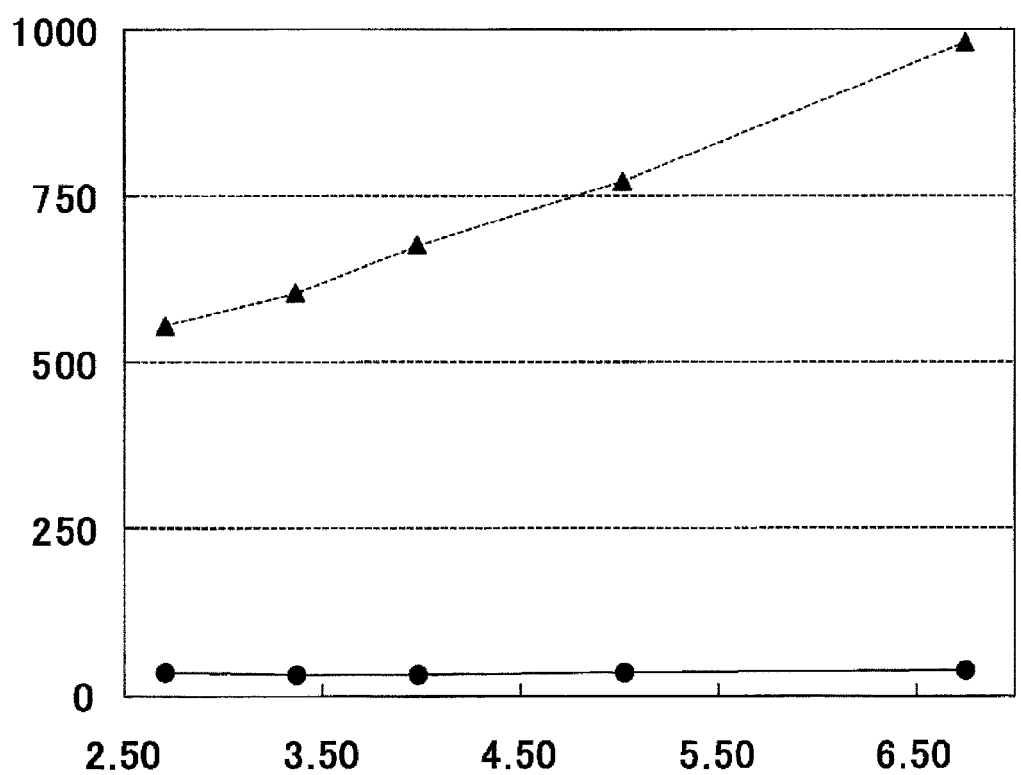
FIG. 4 is a graph showing the relationship between HbA1c concentration and reaction absorbance in the measurement of HbA1c in a sample using kits of Example 4 and Comparative Example 1. The symbol ▲ represents the results of measurement using the kit of Example 4. The symbol ● represents the results of measurement using the kit of Comparative Example 1. The ordinate represents reaction absorbance ($\times 10^{-4}$ Abs). The abscissa represents the theoretical concentration of HbA1c (μmol/L).

As shown in FIG. 4, no quantitative relationship was found between HbA1c concentration and reaction absorbance for the kit of Comparative Example 1 free from C16TBP, whereas the quantitative relationship was found between HbA1c concentration and reaction absorbance for the kit of Example 4 comprising C16TBP. It proved that use of the kit of Example 4 enabled measurement of HbA1c in a sample.

Example 11

The reaction absorbance for each sample was calculated in the same way as in Example 7 except that the kit of Example 5 was used instead of the kit of Example 1 used in Example 7. The relationship between HbA1c concentration and $\Delta E$ is shown as to each sample in FIG. 5.

Figure 5:
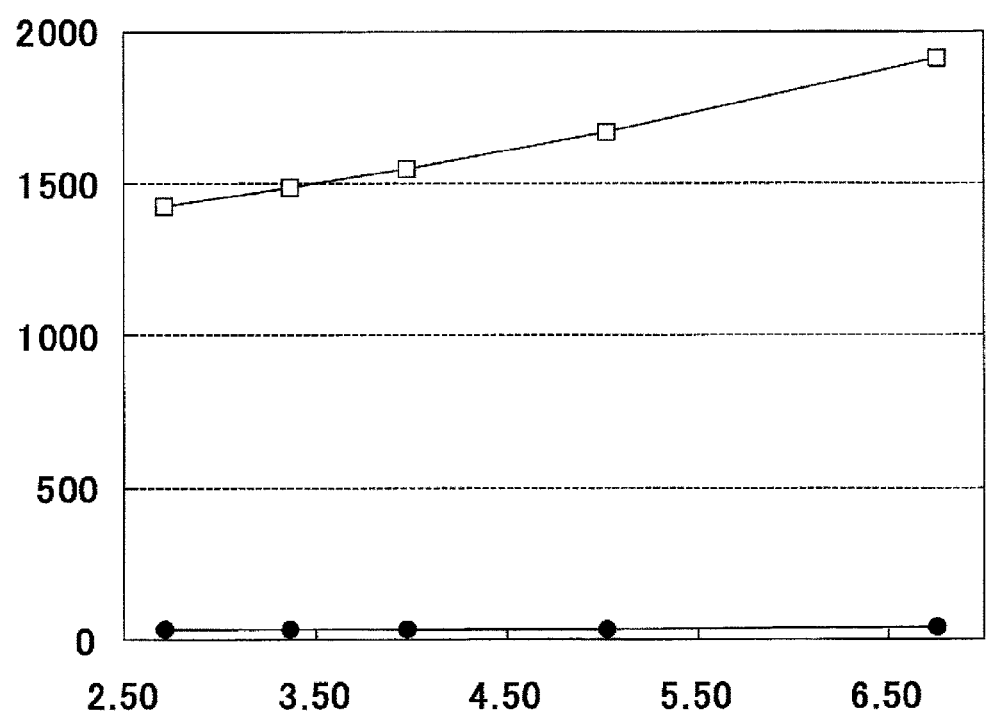
FIG. 5 is a graph showing the relationship between HbA1c concentration and reaction absorbance in the measurement of HbA1c in a sample using kits of Example 5 and Comparative Example 1. The symbol □ represents the results of measurement using the kit of Example 5. The symbol ● represents the results of measurement using the kit of Comparative Example 1. The ordinate represents reaction absorbance ($\times 10^{-4}$ Abs). The abscissa represents the theoretical concentration of HbA1c (μmol/L).

As shown in FIG. 5, no quantitative relationship was found between HbA1c concentration and reaction absorbance for the kit of Comparative Example 1 free from C12 MBI, whereas the quantitative relationship was found between HbA1c concentration and reaction absorbance for the kit of Example 5 comprising C12 MBI. It proved that use of the kit of Example 5 enabled measurement of HbA1c in a sample.

Example 12

The reaction absorbance for each sample was calculated in the same way as in Example 7 except that the kit of Example 6 was used instead of the kit of Example 1 used in Example 7. The relationship between HbA1c concentration and ΔE is shown as to each sample in FIG. 6.

Figure 6:
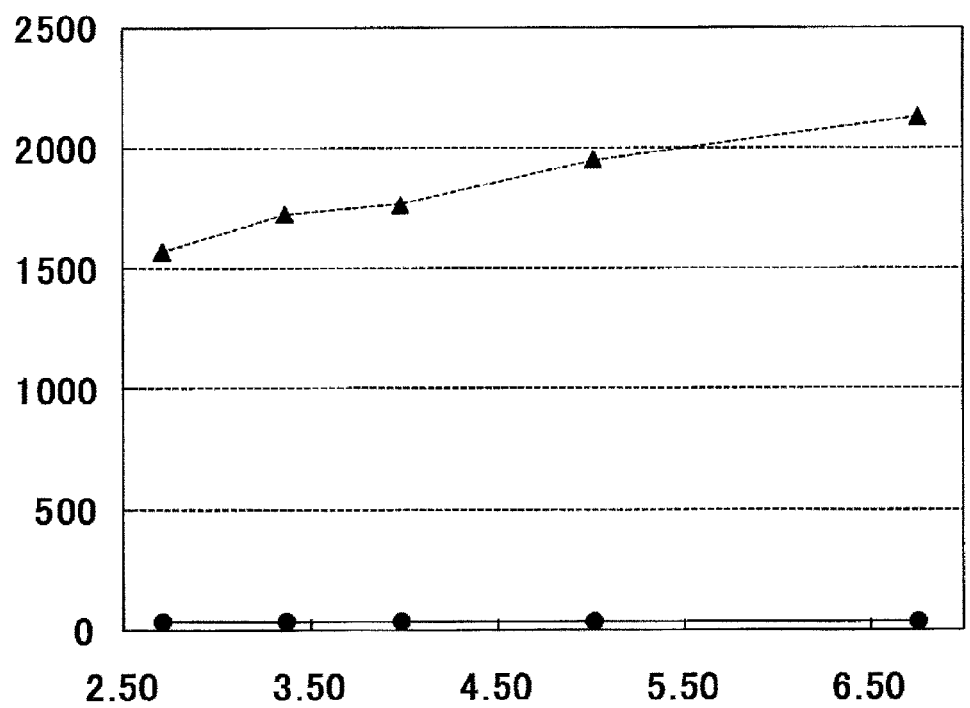
FIG. 6 is a graph showing the relationship between HbA1c concentration and reaction absorbance in the measurement of HbA1c in a sample using kits of Example 6 and Comparative Example 1. The symbol ▲ represents the results of measurement using the kit of Example 6. The symbol ● represents the results of measurement using the kit of Comparative Example 1. The ordinate represents reaction absorbance ($\times 10^{-4}$ Abs). The abscissa represents the theoretical concentration of HbA1c (μmol/L).

As shown in FIG. 6, no quantitative relationship was found between HbA1c concentration and reaction absorbance for the kit of Comparative Example 1 free from Firet Q, whereas the quantitative relationship was found between HbA1c concentration and reaction absorbance for the kit of Example 6 comprising Firet Q. It proved that use of the kit of Example 6 enabled measurement of HbA1c in a sample.

Example 13

A kit for HbA1c measurement consisting of the following first and second reagents was prepared.

| First reagent | |
| --- | --- |
| MES (pH 6.0) | 10 mmol/L |
| C16py | 0.35 g/L |
| Calcium acetate monohydrate | 10 mmol/L |
| Actinase AS | 450 kU/L |
| DA-67 | 20 μmol/L |
| Second reagent | |
| ADA (pH 7.0) | 50 mmol/L |
| FPOX-CE | 12 kU/L |
| Peroxidase | 120 kU/L |

Comparative Example 3

A kit for HbA1c measurement consisting of the following first and second reagents was prepared.

| First reagent | |
| --- | --- |
| MES (pH 6.0) | 10 mmol/L |
| Calcium acetate monohydrate | 10 mmol/L |
| Actinase AS | 450 kU/L |
| DA-67 | 20 μmol/L |
| Second reagent | |
| ADA (pH 7.0) | 50 mmol/L |
| FPOX-CE | 12 kU/L |
| Peroxidase | 120 kU/L |

Example 14

The kit of Example 13 was used as a kit for HbA1c measurement. Blood cells obtained by the centrifugation of human blood were hemolyzed by dilution with deionized water to prepare samples. Hemolyzed samples with an HbA1c concentration valued at 2.5 μmol/L, 3.7 μmol/L, 4.0 μmol/L, 4.7 μmol/L, or 6.3 μmol/L by immunoassay using "Determiner L HbA1c" (manufactured by Kyowa Medex Co., Ltd.) and the SLS-hemoglobin method, which is one of hemoglobin measurements, were used to determine the reaction absorbance for each sample by the following procedures:

9.6 μL of each sample and 120 μL of the first reagent in the kit of Example 1 were added to a reaction cuvette and incubated at 37° C. for 5 minutes (first reaction). The absorbance (E1) of the reaction solution was determined at a primary wavelength of 660 nm and a secondary wavelength of 800 nm. Subsequently, 40 μL of the second reagent was added to this reaction solution, and the mixture was further incubated at 37° C. for 5 minutes (second reaction). The absorbance (E2) of the reaction solution was determined at a primary wavelength of 660 nm and a secondary wavelength of 800 nm. E1 was subtracted from E2 to calculate an absorbance difference ΔE. The relationship between HbA1c concentration and ΔE is shown as to each sample in FIG. 7.

Comparative Example 4

The reaction absorbance for each sample was calculated in the same way as in Example 14 except that the kit of Comparative Example 3 was used instead of the kit of Example 13 used in Example 14.

Figure 7:
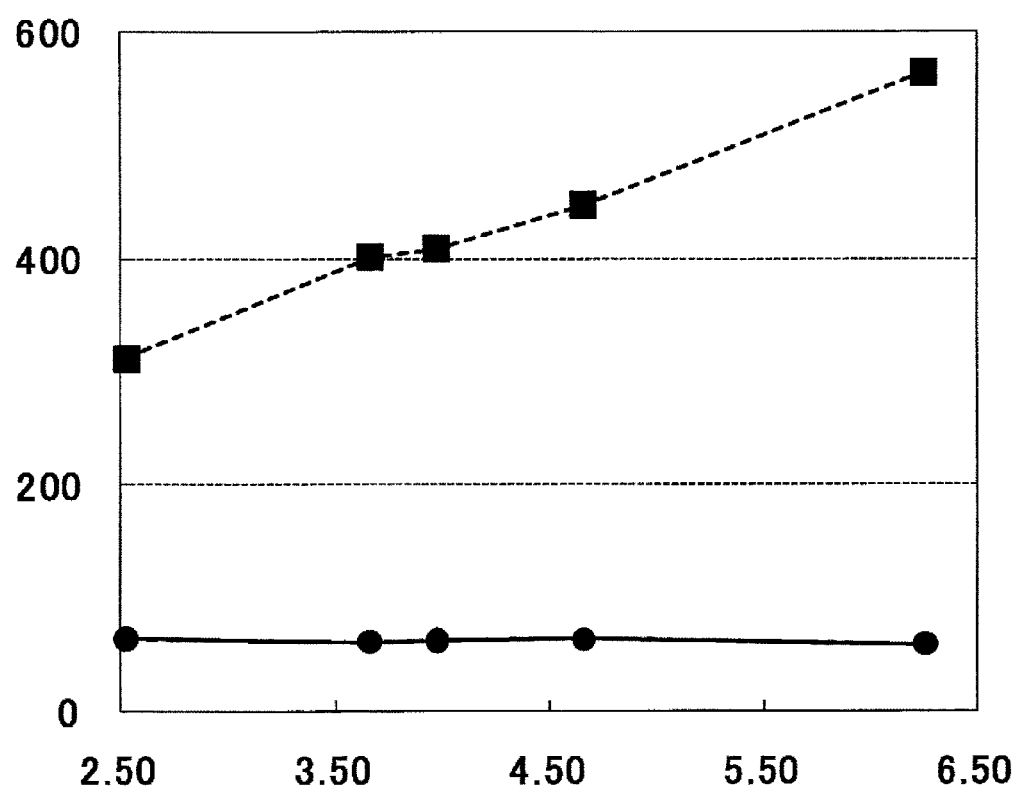
FIG. 7 is a graph showing the relationship between HbA1c concentration and reaction absorbance in the measurement of HbA1c in a sample using kits of Example 13 and Comparative Example 3. The symbol ■ represents the results of measurement using the kit of Example 13. The symbol ● represents the results of measurement using the kit of Comparative Example 3. The ordinate represents reaction absorbance ($\times 10^{-4}$ Abs). The abscissa represents the theoretical concentration of HbA1c (μmol/L).

As shown in FIG. 7, no quantitative relationship was found between HbA1c concentration and reaction absorbance for the kit of Comparative Example 3 free from C16py, whereas the quantitative relationship was found between HbA1c concentration and reaction absorbance for the kit of Example 13 comprising C16py. It proved that use of the kit of Example 13 enabled measurement of HbA1c in a sample.

Example 15

A kit for HbA1c measurement consisting of the following first and second reagents was prepared.

| First reagent | |
| --- | --- |
| Bis-Tris (pH 7.0) | 10 mmol/L |
| C12py | 1.6 g/L |
| Calcium chloride dihydrate | 10 mmol/L |
| Thermolysin | 1200 kU/L |
| DA-67 | 20 μmol/L |
| Second reagent | |
| ADA (pH 7.0) | 50 mmol/L |
| FPOX-CE | 12 kU/L |
| Peroxidase | 120 kU/L |

Example 16

A kit for HbA1c measurement consisting of the following first and second reagents was prepared.

| First reagent | |
| --- | --- |
| Bis-Tris (pH 7.0) | 10 mmol/L |
| C12TBP | 0.8 g/L |
| Calcium chloride dihydrate | 10 mmol/L |
| Thermolysin | 1200 kU/L |
| DA-67 | 20 μmol/L |
| Second reagent | |
| ADA (pH 7.0) | 50 mmol/L |
| FPOX-CE | 12 kU/L |
| Peroxidase | 120 kU/L |

Example 17

A kit for HbA1c measurement consisting of the following first and second reagents was prepared.

| First reagent | |
| --- | --- |
| Bis-Tris (pH 7.0) | 10 mmol/L |
| C12MBI | 0.9 g/L |
| Calcium chloride dihydrate | 10 mmol/L |
| Thermolysin | 1200 kU/L |
| DA-67 | 20 µmol/L |
| Second reagent | |
| ADA (pH 7.0) | 50 mmol/L |
| FPOX-CE | 12 kU/L |
| Peroxidase | 120 kU/L |

Example 18

The kit of Example 15 was used as a kit for HbA1c measurement. Whole blood derived from 10 test subjects suspected of having diabetes mellitus was used as a sample to determine the ratio [HbA1c (%)] of HbA1c concentration (amount) to total hemoglobin concentration (amount) in each sample by the following procedures:
(1) Preparation of Calibration Curve for Determining Total Hemoglobin Concentration "Hemoglobin B-Test Wako" (SLS-hemoglobin method) (manufactured by Wako Pure Chemical Industries, Ltd.) was used as a kit for total hemoglobin measurement. A standard (hemoglobin concentration: 15.3 mg/mL) included in "Hemoglobin B-Test Wako" was used as a specimen in measurement to prepare a calibration curve showing the relationship between hemoglobin concentration and absorbance.
(2) Preparation of Calibration Curve for Determining HbA1c Concentration For each of two blood cell fractions with HbA1c concentrations valued at 2.77 µmol/L and 6.33 µmol/L, respectively, by latex immunoagglutination assay, the measurement was performed using the kit for HbA1c measurement of Example 15 to determine the absorbance for each blood cell fraction. Saline was used instead of the blood cell fraction to determine the HbA1c concentration for the saline. The absorbance for the saline was subtracted from the absorbance for each blood cell fraction, and the value thus calculated was used as the blank-corrected absorbance for the blood cell fraction. A calibration curve showing the relationship between HbA1c concentration (µmol/L) and absorbance was prepared from the blank-corrected absorbance for the blood cell fraction and the blank-corrected absorbance (0 Abs) for the saline.
(3) Determination of Hemoglobin Concentration in Each Blood Cell Fraction Each sample was centrifuged at 3000 rpm at 25° C. for 5 minutes to obtain a blood cell fraction. For each blood cell fraction, the measurement was performed using "Hemoglobin B-Test Wako", and the hemoglobin concentration (µmol/L) in each blood cell fraction was determined from the obtained measurement value and the calibration curve prepared in the paragraph (1).
(4) Determination of HbA1c Concentration in Each Blood Cell Fraction For each blood cell fraction, the measurement was performed using the measurement kit of the present invention, and the HbA1c concentration (µmol/L) in each blood cell fraction was determined from the obtained measurement value and the calibration curve prepared in the paragraph (2).
(5) Determination of HbA1c (%) (=Ratio of HbA1c Concentration to Hemoglobin Concentration)

HbA1c (%) was calculated as a Japan Diabetes Society (JDS) value according to the following formula from the hemoglobin concentration (µmol/L) in each blood cell fraction determined in the paragraph (3) and the HbA1c concentration (µmol/L) in each blood cell fraction determined in the paragraph (4):

HbA1c(%)=[HbA1c concentration (µmol/L)]/[Hemoglobin concentration (µmol/L)]×0.0963+1.62  [Equation 1]

(6) Determination of HbA1c (%) in Same Blood Cell Fraction by Immunoassay

The same blood cell fractions as those used in the determination of HbA1c (%) in the paragraph (5) were used. HbA1c (%) in each blood cell fraction was determined by immunoassay using "Determiner L HbA1c" (manufactured by Kyowa Medex Co., Ltd.) according to the protocol described in the attachment of "Determiner L HbA1c".
(7) Correlation Between Measuring Method of the Present Invention and Immunoassay The correlation between the measuring method of the present invention and immunoassay was verified from HbA1c (%) determined in the paragraph (5) using the measuring method of the present invention and HbA1c (%) determined in the paragraph (6) using the immunoassay to determine a correlation coefficient.

As a result, the correlation coefficient between both the measuring methods was 0.994, showing the favorable correlation between these measuring methods. These results demonstrated that the measuring method of the present invention using the kit of Example 15 could accurately measure HbA1c in a sample.

Example 19

The correlation coefficient between the measuring method of the present invention and measurement using "Determiner L HbA1c" (manufactured by Kyowa Medex Co., Ltd.) was determined by the same procedures as in Example using the kit of Example 16 instead of the kit of Example 15. As a result, the correlation coefficient was 0.984, showing the favorable correlation between both the measuring methods. These results demonstrated that the measuring method of the present invention using the kit of Example 16 could accurately measure HbA1c in a sample.

Example 20

The correlation coefficient between the measuring method of the present invention and measurement using "Determiner L HbA1c" (manufactured by Kyowa Medex Co., Ltd.) was determined by the same procedures as in Example using the kit of Example 17 instead of the kit of Example 15. As a result, the correlation coefficient was 0.949, showing the favorable correlation between both the measuring methods. These results demonstrated that the measuring method of the present invention using the kit of Example 17 could accurately measure HbA1c in a sample.

Example 21

(1) Preparation of Aqueous Solution Containing DA-67 and Sample for DA-67 Stability Assay An aqueous solution containing DA-67 was prepared according to the following composition:

| <Aqueous solution containing DA-67> | |
| --- | --- |
| Bis-Tris (pH 7.0) | 10 mmol/L |
| DA-67 | 20 µmol/L |
| Surfactant (see Table 1) | 0.5% |

Each DA-67-containing aqueous solution having this composition was stored at 5° C. for 7 days or at 30° C. for 7 days. The resulting solutions were used as samples for DA-67 stability assay.

(2) Preparation of Reagent for DA-67 Stability Assay

A reagent for DA-67 stability assay was prepared according to the following composition:

| <Reagent for DA-67 stability assay> | |
|---|---|
| Bis-Tris (pH 7.0) | 10 mmol/L |
| BSA | 0.005% |

(3) Evaluation of Stability of DA-67 in DA-67-Containing Aqueous Solution

120 μL of the reagent for DA-67 stability assay prepared in the paragraph (2) was added to 30 μL of the freshly-prepared DA-67-containing aqueous solution, and the mixture was heated at 37° C. for 5 minutes. Then, the absorbance ($E_{freshly\text{-}prepared}$) of the solution was measured at a primary wavelength of 660 nm and a secondary wavelength of 800 nm using Hitachi 7170S automatic analyzer. The same assay was conducted using the reagent for DA-67 stability assay of (2) instead of the freshly-prepared DA-67-containing aqueous solution to determine its absorbance ($E_{blank}$). $E_{blank}$ was subtracted from $E_{freshly\text{-}prepared}$ to determine the absorbance ($\Delta E_{freshly\text{-}prepared}$) of the freshly-prepared DA-67-containing aqueous solution.

Similarly, the DA-67-containing aqueous solution stored at 5° C. for 7 days and the DA-67-containing aqueous solution stored at 30° C. for 7 days were assayed as samples to determine the absorbance ($\Delta E_{5° C.}$) for the DA-67-containing aqueous solution stored at 5° C. for 7 days and the absorbance ($\Delta E_{30° C.}$) for the DA-67-containing aqueous solution stored at 30° C. for 7 days.

$\Delta E_{freshly\text{-}prepared}$ was subtracted from each of $\Delta E_{5° C.}$ and $\Delta E_{30° C.}$ thus determined. The determined values were designated as $\Delta E_1$ and $\Delta E_2$, respectively, and used as indexes for the stability of DA-67. The results are shown in Table 1. A value closer to 0 represents that the aqueous solution is prevented from being colored and DA-67 is stably preserved in the aqueous solution, i.e., DA-67 is stabilized in the aqueous solution.

TABLE 1

| | Change in absorbance after 7-day storage | |
|---|---|---|
| Surfactant | $\Delta E_1$ (Stored at 5° C.) | $\Delta E_2$ (Stored at 30° C.) |
| — | 0.002 | 0.023 |
| C12py | 0.003 | 0.009 |
| C16py | 0.005 | 0.006 |
| C12TBP | 0.005 | 0.005 |
| C16TBP | 0.000 | 0.004 |

As shown in Table 1, the aqueous solution comprising compound (I) (C12py or C16py) was significantly prevented from being colored after storage both at 5° C. and at 30° C., compared with the aqueous solution free from compound (I). It proved that DA-67 in the aqueous solution comprising compound (I) was stable against heat and the DA-67-containing aqueous solution was stably preserved by compound (I), i.e., DA-67 was stabilized in the aqueous solution by compound (I).

Similarly, the aqueous solution comprising compound (II) (C12TBP or C16TBP) was significantly prevented from being colored after storage both at 5° C. and at 30° C., compared with the aqueous solution free from compound (II). It proved that DA-67 in the aqueous solution comprising compound (II) was stable against heat and the DA-67-containing aqueous solution was stably preserved by compound (II), i.e., DA-67 was stabilized in the aqueous solution by compound (II).

Example 22

The DA-67-containing aqueous solution prepared in Example 21 was irradiated with 1100 lux of light for 15 hours to evaluate the light stability of DA-67. The DA-67-containing aqueous solution immediately after light irradiation was used as a sample in the same way as in Example 21 to determine the absorbance $\Delta E_3$ of the DA-67-containing aqueous solution after light irradiation. The assay results are shown in Table 2.

TABLE 2

| Surfactant | $\Delta E_3$ (Change in absorbance after 15-hr light irradiation) |
|---|---|
| — | 0.064 |
| C12py | 0.010 |
| C16py | 0.000 |
| C12TBP | 0.000 |
| C16TBP | 0.000 |

As shown in Table 2, the aqueous solution comprising compound (I) (C12py or C16py) was significantly prevented from being colored due to light irradiation, compared with the aqueous solution free from compound (I). It proved that DA-67 in the aqueous solution comprising compound (I) was stable against light and the DA-67-containing aqueous solution was stably preserved by compound (I), i.e., DA-67 was stabilized in the aqueous solution by compound (I).

Similarly, the aqueous solution comprising compound (II) (C12TBP or C16TBP) was significantly prevented from being colored due to light irradiation, compared with the aqueous solution free from compound (II). It proved that DA-67 in the aqueous solution comprising compound (II) was stable against light and the DA-67-containing aqueous solution was stably preserved by compound (II), i.e., DA-67 was stabilized in the aqueous solution by compound (II).

INDUSTRIAL APPLICABILITY

The present invention provides a method, a reagent, and a kit for measuring glycated hemoglobin in a hemoglobin-containing sample. In addition, the present invention provides a method for preserving an aqueous solution containing a leuco chromogen, and a method for stabilizing a leuco chromogen. The method, the reagent and the kit of the present invention are useful in, for example, measurement of glycated hemoglobin used in the diagnosis of diabetes mellitus.

The invention claimed is:
1. A method for measuring glycated hemoglobin in a hemoglobin-containing sample, comprising: reacting the glycated hemoglobin in the hemoglobin-containing sample with a proteolytic enzyme in the presence of a pyridinium salt represented by the following formula (I) to obtain a reaction product comprising a glycated peptide; reacting the obtained reaction product with fructosyl peptide oxidase to generate hydrogen peroxide; and measuring the generated hydrogen peroxide:

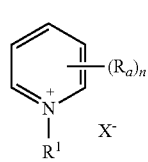

(I)

wherein $R^1$ represents a substituted or unsubstituted alkyl or a substituted or unsubstituted alkenyl; $R_a$ represents a hydrogen atom, a substituted or unsubstituted alkyl, or a substituted or unsubstituted alkenyl; n represents an integer of 1 to 5; and $X^-$ represents a monovalent anion.

2. The method according to claim 1, wherein the measuring hydrogen peroxide is performed by adding a hydrogen peroxide measuring agent to the generated hydrogen peroxide.

3. The method according to claim 2, wherein the hydrogen peroxide measuring reagent is a reagent comprising peroxidase and a leuco chromogen.

4. The method according to claim 3, wherein the leuco chromogen is a phenothiazine chromogen.

5. The method according to claim 4, wherein the phenothiazine chromogen is 10-(carboxymethylaminocarbonyl)-3,7-bis(dimethylamino)phenothiazine.

* * * * *

UNITED STATES PATENT AND TRADEMARK OFFICE
CERTIFICATE OF CORRECTION

PATENT NO. : 9,090,931 B2  
APPLICATION NO. : 13/811914  
DATED : July 28, 2015  
INVENTOR(S) : Haruyo Soya et al.

Page 1 of 1

It is certified that error appears in the above-identified patent and that said Letters Patent is hereby corrected as shown below:

ON TITLE PAGE AT (56) REFERENCES CITED:

"WO WO 2007072941 A * 6/2007" should read --WO 2007/072941 A * 6/2007--.

IN THE SPECIFICATION:

COLUMN 12:

Line 55, "represent" should read --represents--.

COLUMN 13:

Line 51, "represent" should read --represents--.

COLUMN 16:

Line 15, "hour." should read --1 hour.--.

COLUMN 20:

Line 34, "that" should read --that the--;  
Line 35, "larger" should read --the larger--; and  
Line 38, "weaker" should read --the weaker-- and "smaller" should read --the smaller--.

IN THE CLAIMS:

COLUMN 31:

Line 19, "measuring" should read --measuring of the generated--.

Signed and Sealed this  
Fifteenth Day of March, 2016

Michelle K. Lee  
*Director of the United States Patent and Trademark Office*